United States Patent
Hammud et al.

(10) Patent No.: US 11,840,545 B1
(45) Date of Patent: Dec. 12, 2023

(54) SPIROOXINDOLE-COPPER COMPLEX AS NOVEL EFFICIENT ANTICORROSION AGENT FOR C-STEEL

(71) Applicant: KING FAISAL UNIVERSITY, Al-Ahsa (SA)

(72) Inventors: Hassan H. Hammud, Al-Ahsa (SA); Waleed A. S. Aljamhi, Al-Ahsa (SA); Ayman El-Faham, Al-Ahsa (SA); Assem Barakat, Al-Ahsa (SA); Ihab Shawish, Al-Ahsa (SA); Nadeem S. Sheikh, Al-Ahsa (SA); Khurshid Ayub, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/222,277

(22) Filed: Jul. 14, 2023

(51) Int. Cl.
*C07D 513/20* (2006.01)
*C07F 1/08* (2006.01)

(52) U.S. Cl.
CPC .............. *C07D 513/20* (2013.01); *C07F 1/08* (2013.01)

(58) Field of Classification Search
None
See application file for complete search history.

(56) References Cited

U.S. PATENT DOCUMENTS 8,742,109 B2   6/2014   Cadieux et al.
8,916,580 B2 * 12/2014   Chafeev .................... A61P 1/04
                                                        546/15

FOREIGN PATENT DOCUMENTS

CA        2777543 A1    4/2011

OTHER PUBLICATIONS

Altowyan et al., "[3+2] Cycloaddition Reaction for the Stereoselective Synthesis of a New Spirooxindole Compound Grafted Imidazo[2,1-b]thiazole Scaffold: Crystal Structure and Computational Study", Crystals 2022, 12(1), 5.
Kumar et al., "Sustainable synthesis of highly diastereoselective & fluorescent active spirooxindoles catalyzed by copper oxide nanoparticle immobilized on microcrystalline cellulose", Applied Organometallic Chemistry, vol. 36, Issue 7, Jul. 2022.

* cited by examiner

*Primary Examiner* — Joseph R Kosack
(74) *Attorney, Agent, or Firm* — Nath, Goldberg & Meyer; Richard C. Litman

(57) ABSTRACT

New spirooxindole compounds are described herein, as well as the use of such spirooxindole compounds in forming copper complexes that act as efficient anticorrosion agents for C-steel. Also described are methods for forming the new spirooxindole compounds as well as anti-corrosion coatings containing the spirooxindole-copper complexes, CuL.

16 Claims, 23 Drawing Sheets

SPIROOXINDOLE-COPPER COMPLEX AS NOVEL EFFICIENT ANTICORROSION AGENT FOR C-STEEL

BACKGROUND

Field

The disclosure of the present patent application relates to new spirooxindole compounds, and particularly to the use of such spirooxindole compounds in forming copper complexes that act as efficient anticorrosion agents for C-steel.

Description of Related Art

Corrosion is a loss of material due to physical, chemical, electro-chemical or biological reaction with the environment. The use of anti-corrosive coatings and linings has become a necessity to safeguard huge investments in terms of money and property. The demand for efficient anti-corrosion coatings is continuously increasing. The anti-corrosive coatings should protect metal surfaces from degradation due to air and moisture oxidation, prevent direct contact of environmental chemical hazards, act as a barrier from corrosive materials, prolong their structural life and efficiency.

Thus, new anti-corrosive materials apparatus solving the aforementioned problems are desired.

SUMMARY

The present subject matter relates to new phenyl spirooxindole derivatives that can be used as a ligand L to prepare a copper complex. The complex CuL can have much higher anticorrosion inhibitory effects than its ligand for C-steel, for example, in 1 M HCl solution.

Accordingly, in one embodiment, the present subject matter relates to a compound of the formula I:

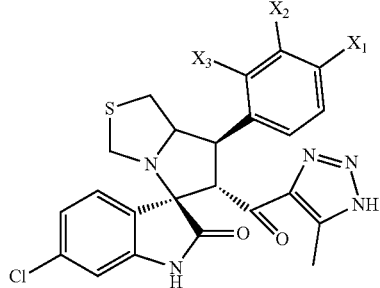

wherein $X_1$, $X_2$, and $X_3$ are each independently selected from the group consisting of chlorine, hydrogen, $NO_2$, and bromine.

In another embodiment, the present subject matter relates to a copper complex comprising a complex of the formula II:

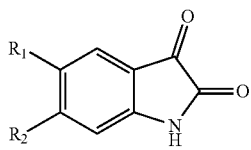

wherein L is a ligand that is the compounds as described herein.

In a further embodiment, the present subject matter relates to a method for making the copper complex as described herein, the method comprising: reacting equimolar amounts of the compound of formula I (ligand L) and copper chloride (CuCl) in an organic solvent; and obtaining the copper complex of formula II (CuL).

In an embodiment, the present subject matter relates to an anticorrosion coating comprising the copper complex as described herein.

In one more embodiment, the present subject matter relates to a method of preventing corrosion in a material, comprising: administering a continuous monolayer of the anticorrosion coating as described herein to a material selected from the group consisting of steel, iron, copper, and a combination thereof.

In a further embodiment, the present subject matter relates to a method of preparing the compound of formula I, the method comprising: adding about one equivalent of (s)-Thiazolidine-4-carboxylic acid to a solution of about one equivalent of a compound of formula III in an organic solvent to obtain a first mixture:

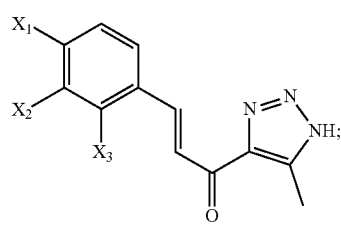

wherein $R_1$ is selected from the group consisting of hydrogen, chlorine, fluorine, bromine, and $NO_2$ and $R_2$ is selected from the group consisting of hydrogen and chlorine; adding a chalcone of formula IV to the first mixture and refluxing for about 6 to about 12 hours to obtain a second mixture:

IV wherein $X_1$, $X_2$, and $X_3$ are each independently selected from the group consisting of chlorine, hydrogen, $NO_2$, and bromine; evaporating the organic solvent from the second mixture to obtain a crude product; and purifying the crude product by column chromatography to obtain the compound of formula I.

In an embodiment, the present subject matter relates to a method of preparing the compound of formula I, the method comprising: adding about one equivalent of 1-(1-(4,6-Dimethoxy-1,3,5-triazin-2-yl)-5-methyl-1H-1,2,3-triazol-4-yl) (B) to ethanol until dissolved; adding an about 7% KOH dropwise with stirring for about 5 minutes to obtain a reaction mixture; placing the reaction mixture in an ice bath and adding a benzaldehyde of formula V with stirring for about 1 to about 2 hours:

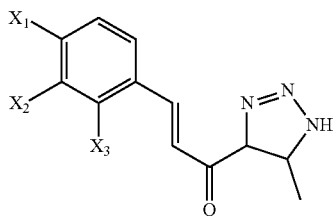

wherein $X_1$, $X_2$, and $X_3$ are each independently selected from the group consisting of chlorine, hydrogen, $NO_2$, and bromine;
evaporating the ethanol and extracting a chalcone of formula IV:

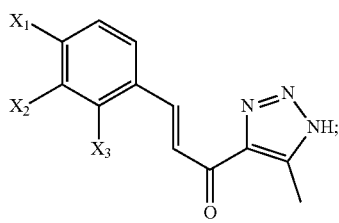

adding one equivalent of (s)-Thiazolidine-4-carboxylic acid to a solution of one equivalent of a compound of formula III in an organic solvent to obtain a first mixture:

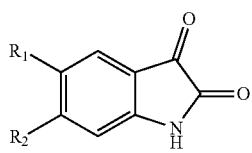

wherein $R_1$ is selected from the group consisting of hydrogen, chlorine, fluorine, bromine, and $NO_2$ and $R_2$ is selected from the group consisting of hydrogen and chlorine; adding the chalcone of formula IV to the first mixture and refluxing for about 6 to about 12 hours to obtain a second mixture; evaporating the organic solvent from the second mixture to obtain a crude product; and purifying the crude product by column chromatography to obtain the compound of formula I.

In one more embodiment, the present subject matter relates to a method of preparing the compound of formula I, the method comprising: adding methanol to cyanuric chloride followed by $NaHCO_3$ with stirring at about 0° C., followed by stirring at room temperature for about 30 minutes, extraction, and drying to obtain 2,4-dichloro-6-methoxy-1,3,5-triazine; dissolving the 2,4-dichloro-6-methoxy-1,3,5-triazine in MeCn followed by adding a solution of sodium azide in water and stirring, first in an ice bath then at room temperature, extraction, concentration, and drying to obtain 2-Azido-4,6-dimethoxy-1,3,5-triazine (A); adding about one equivalent of the 2-Azido-4,6-dimethoxy-1,3,5-triazine (A) to a stirred solution of about 1.2 equivalents of acetylacetone and about 1.2 equivalents of TEA in DMF followed by adding water, filtering, and drying to obtain 1-(1-(4,6-Dimethoxy-1,3,5-triazin-2-yl)-5-methyl-1H-1,2,3-triazol-4-yl) (B); adding about one equivalent of the 1-(1-(4,6-Dimethoxy-1,3,5-triazin-2-yl)-5-methyl-1H-1,2,3-triazol-4-yl) (B) to ethanol until dissolved; adding an about 7% KOH dropwise with stirring for about 5 minutes to obtain a reaction mixture; placing the reaction mixture in an ice bath and adding a benzaldehyde of formula V with stirring for about 1 to about 2 hours:

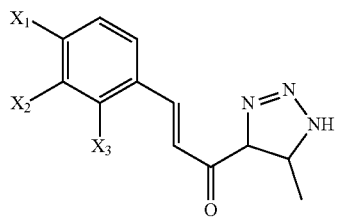

wherein $X_1$, $X_2$, and $X_3$ are each independently selected from the group consisting of chlorine, hydrogen, $NO_2$, and bromine; evaporating the ethanol and extracting a chalcone of formula IV:

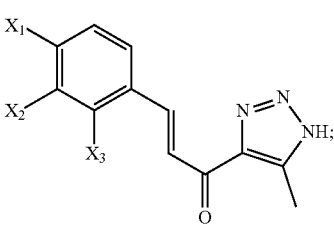

adding one equivalent of (s)-Thiazolidine-4-carboxylic acid to a solution of one equivalent of a compound of formula III in an organic solvent to obtain a first mixture:

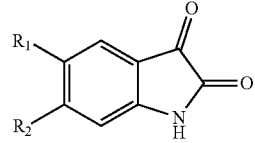

wherein $R_1$ is selected from the group consisting of hydrogen, chlorine, fluorine, bromine, and $NO_2$ and $R_2$ is selected from the group consisting of hydrogen and chlorine; adding the chalcone of formula IV to the first mixture and refluxing for about 6 to about 12 hours to obtain a second mixture; evaporating the organic solvent from the second mixture to obtain a crude product; and purifying the crude product by column chromatography to obtain the compound of formula I.

These and other features of the present subject matter will become readily apparent upon further review of the following specification.

BRIEF DESCRIPTION OF DRAWINGS

(FIG. 20A) Langmuir model, (FIG. 20B) Temkin model, and (FIG. 20C) for (CuL, L=SP 37) Langmuir model.
(FIG. 22A) Langmuir model and (FIG. 22B) Temkin model.

Similar reference characters denote corresponding features consistently throughout the attached drawings.

DETAILED DESCRIPTION

Figure 1A:
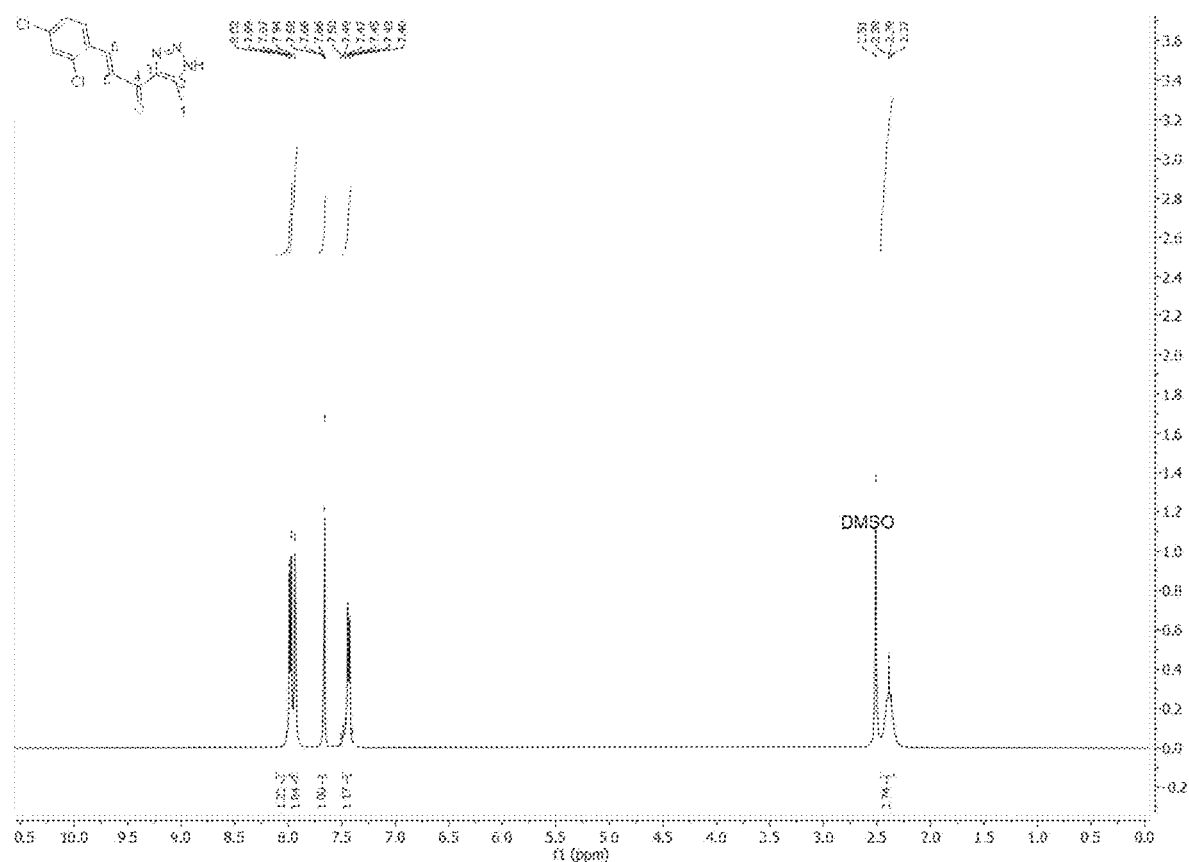
FIG. 1A is a $^1$H-NMR graph of the chalcone d1.
Figure 1B:
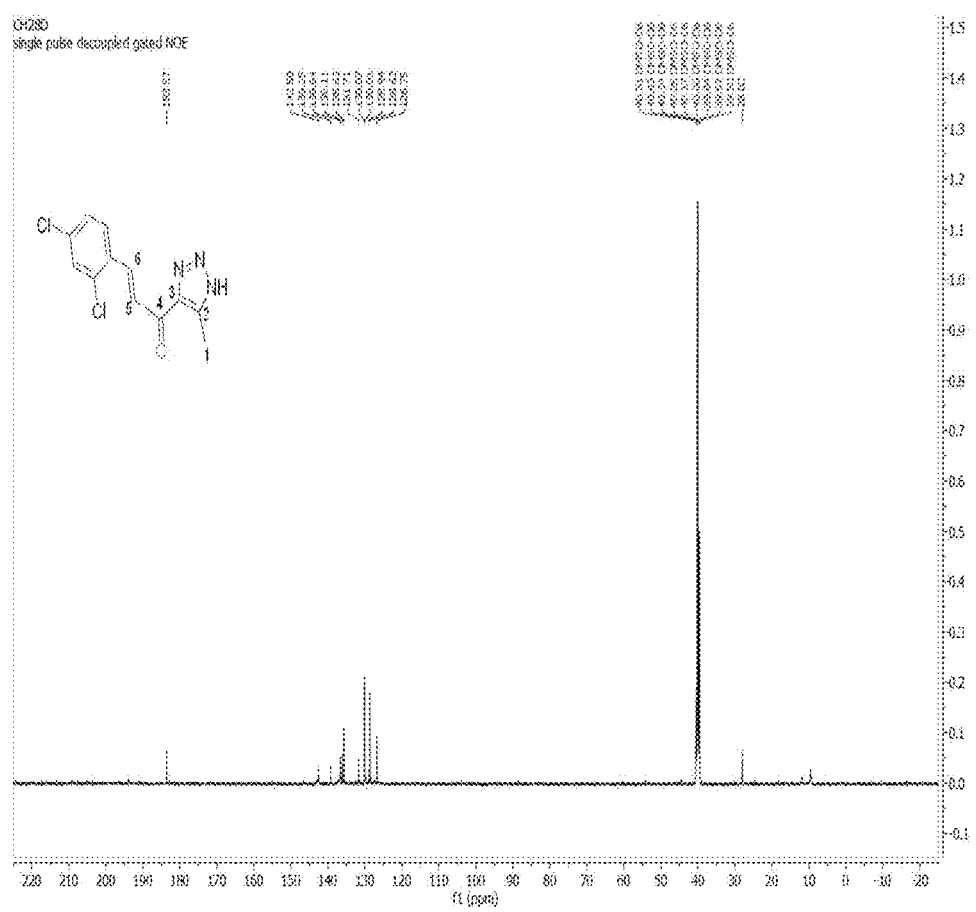
FIG. 1B is a $^{13}$C-NMR graph of the chalcone d1.
Figure 2A:
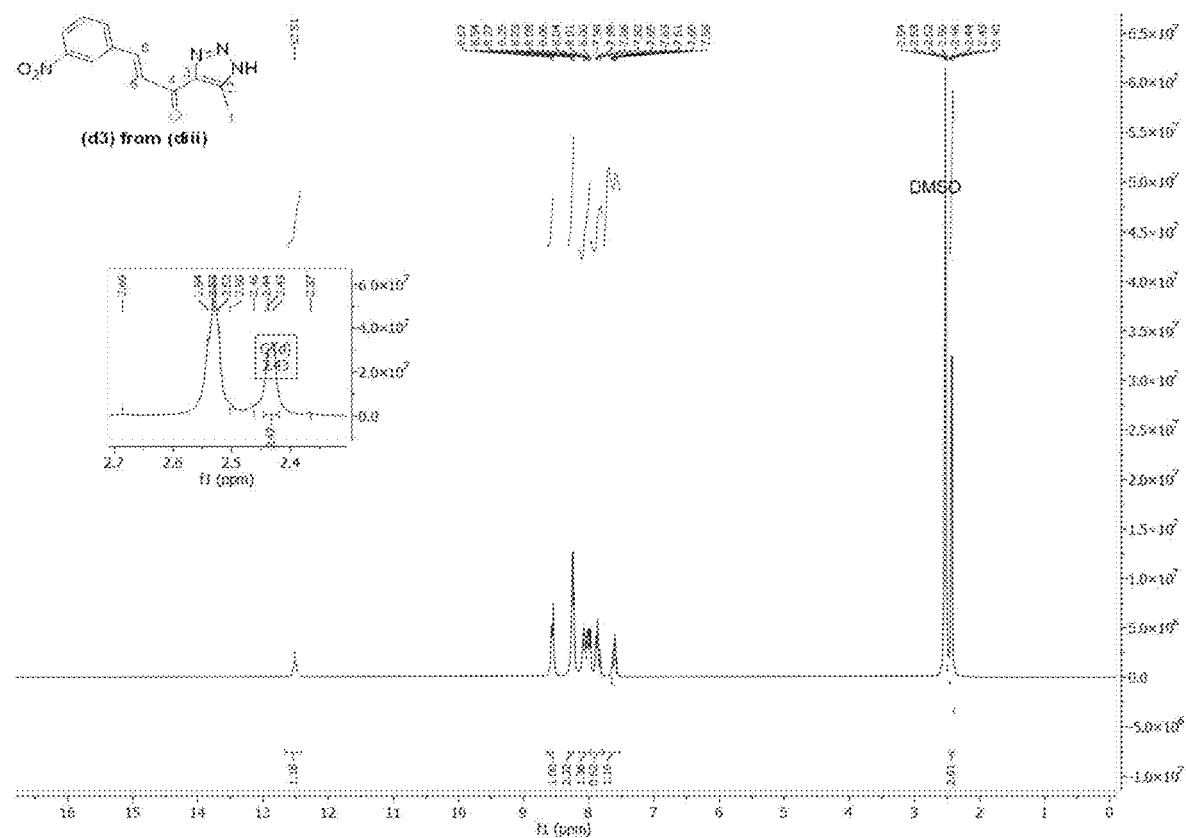
FIG. 2A is a $^1$H-NMR graph of the chalcone d2.
Figure 2B:
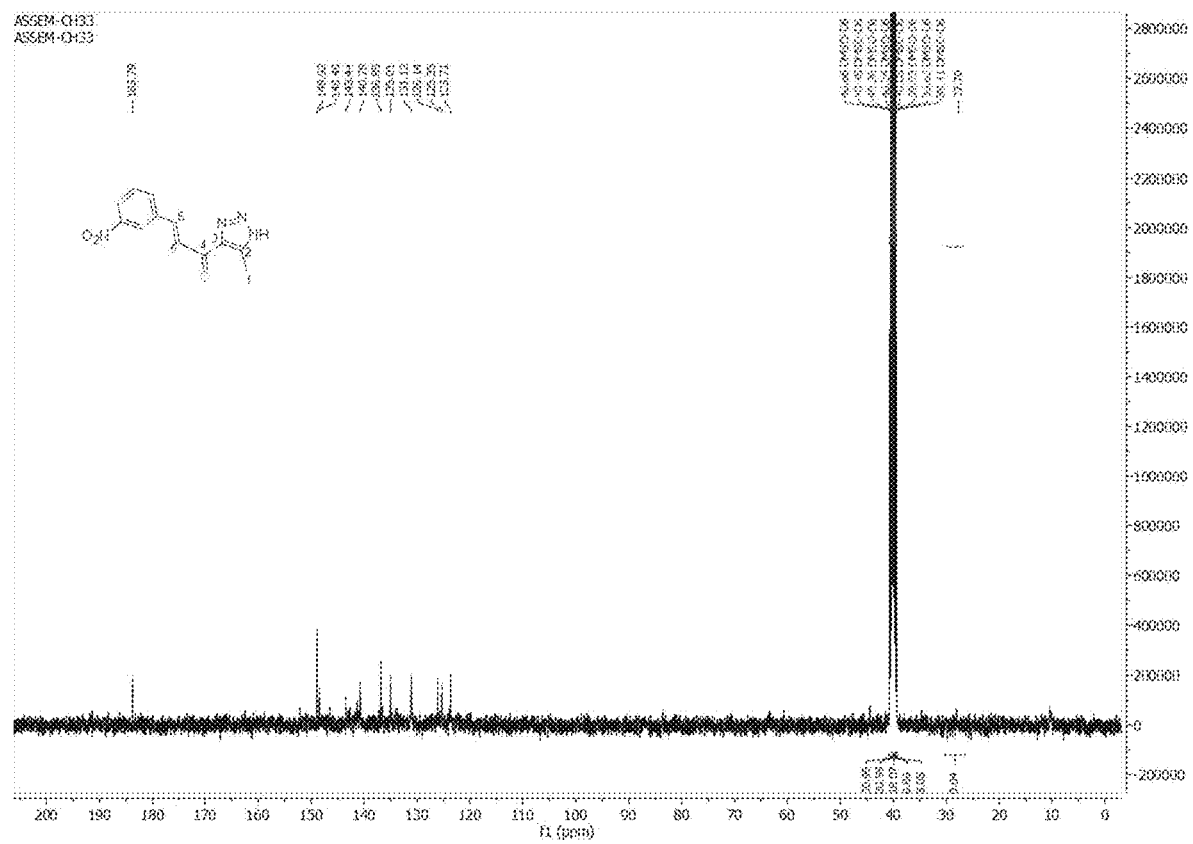
FIG. 2B is a $^{13}$C-NMR graph of the chalcone d2.
Figure 3A:
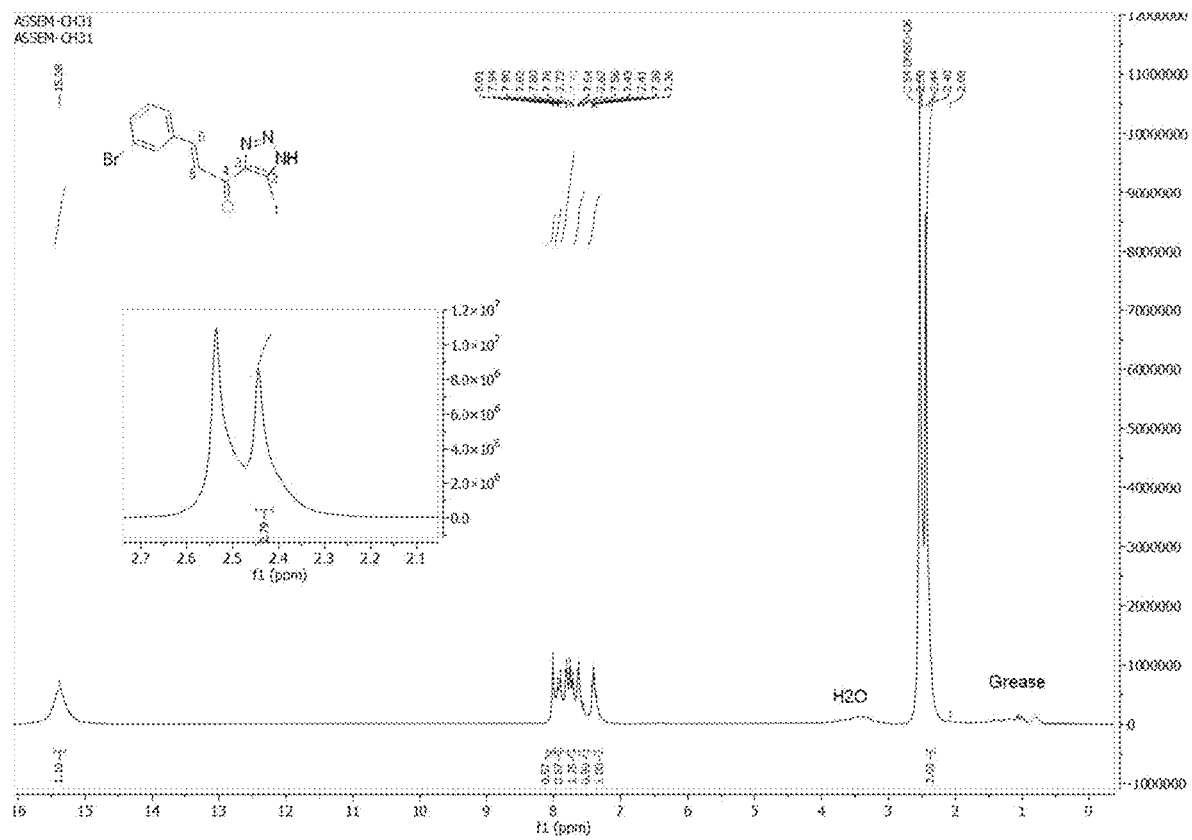
FIG. 3A is a $^1$H-NMR graph of the chalcone d3.
Figure 3B:
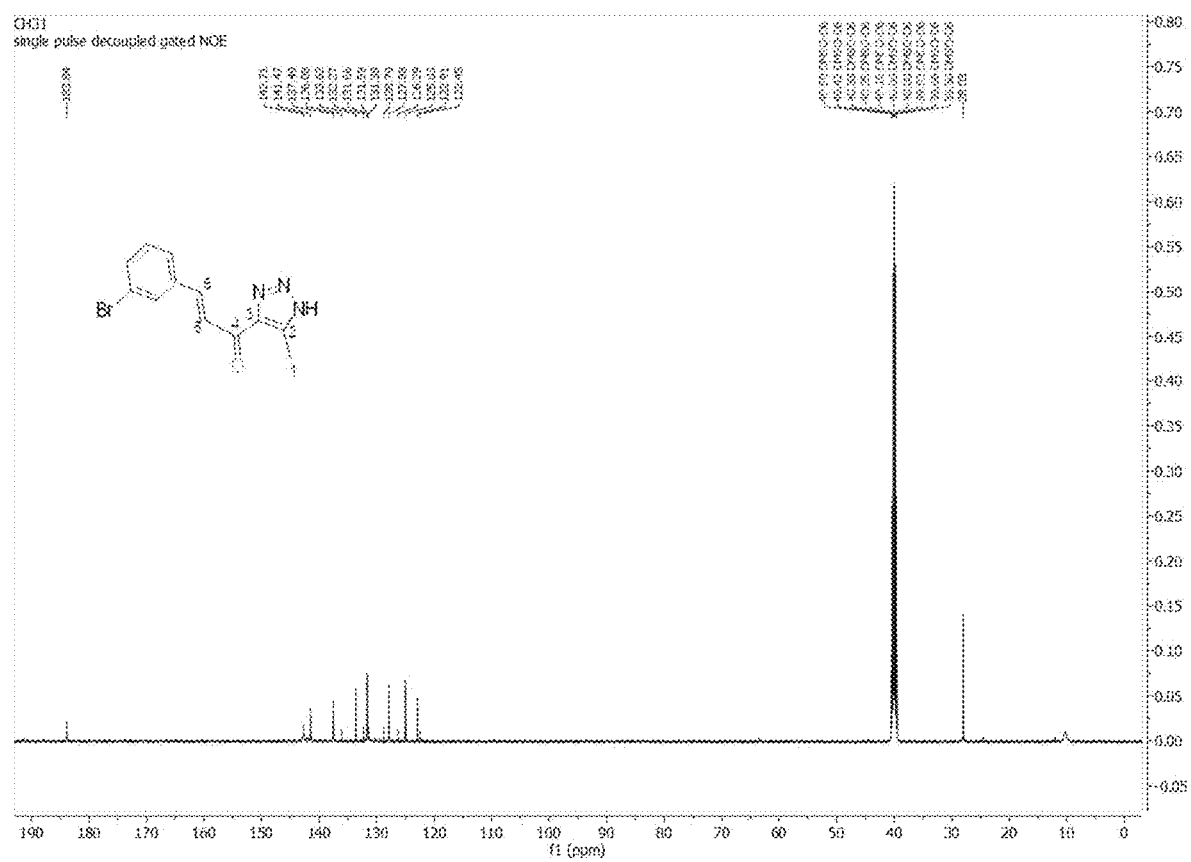
FIG. 3B is a $^{13}$C-NMR graph of the chalcone d3.
Figure 4A:
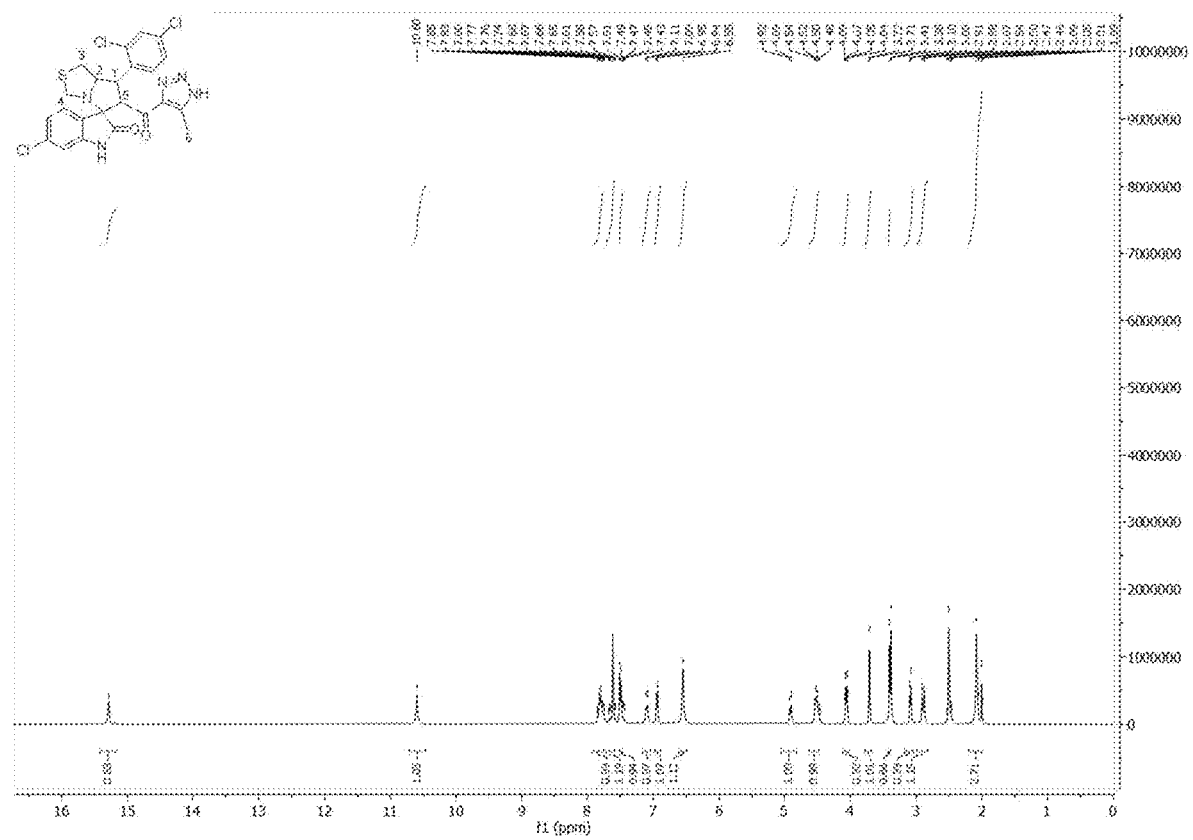
FIG. 4A is a $^1$H-NMR graph of the compound SP34.
Figure 4B:
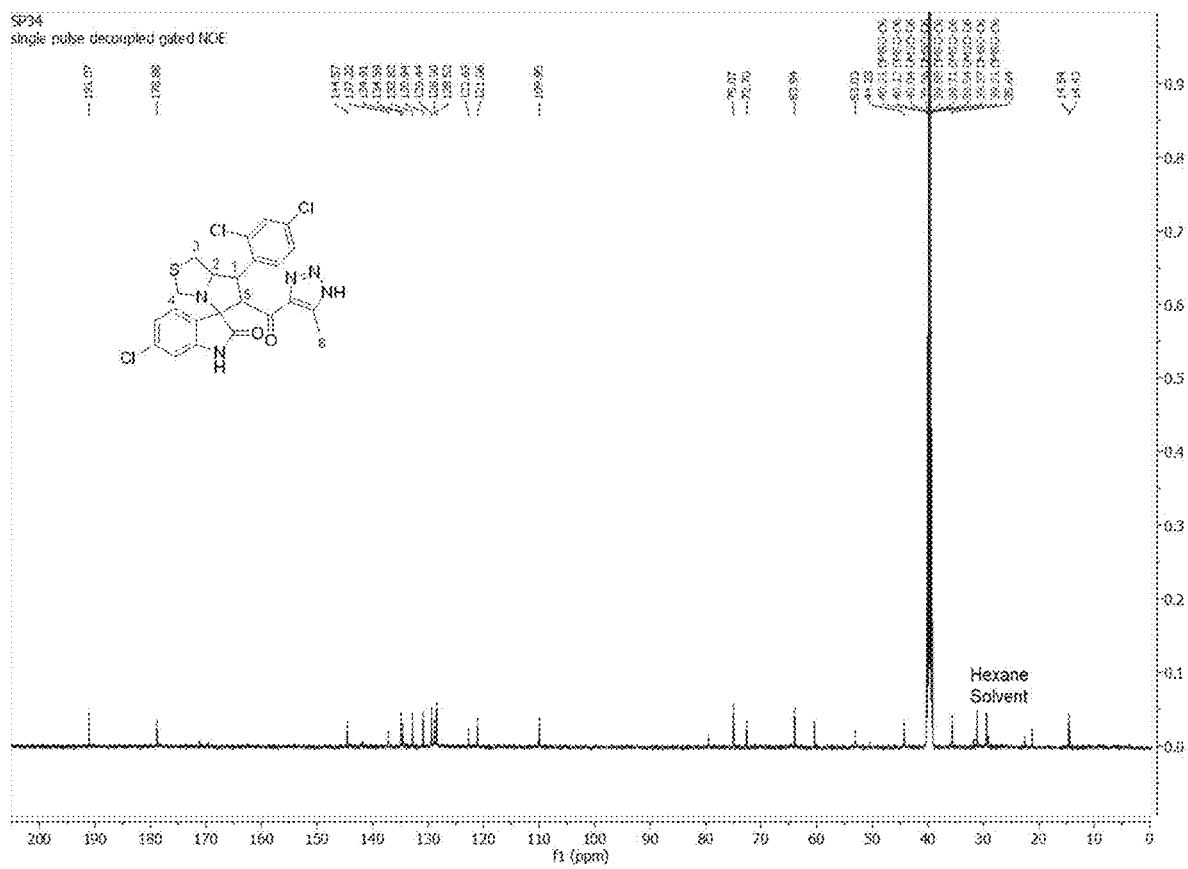
FIG. 4B is a $^{13}$C-NMR graph of the compound SP34.
Figure 5A:
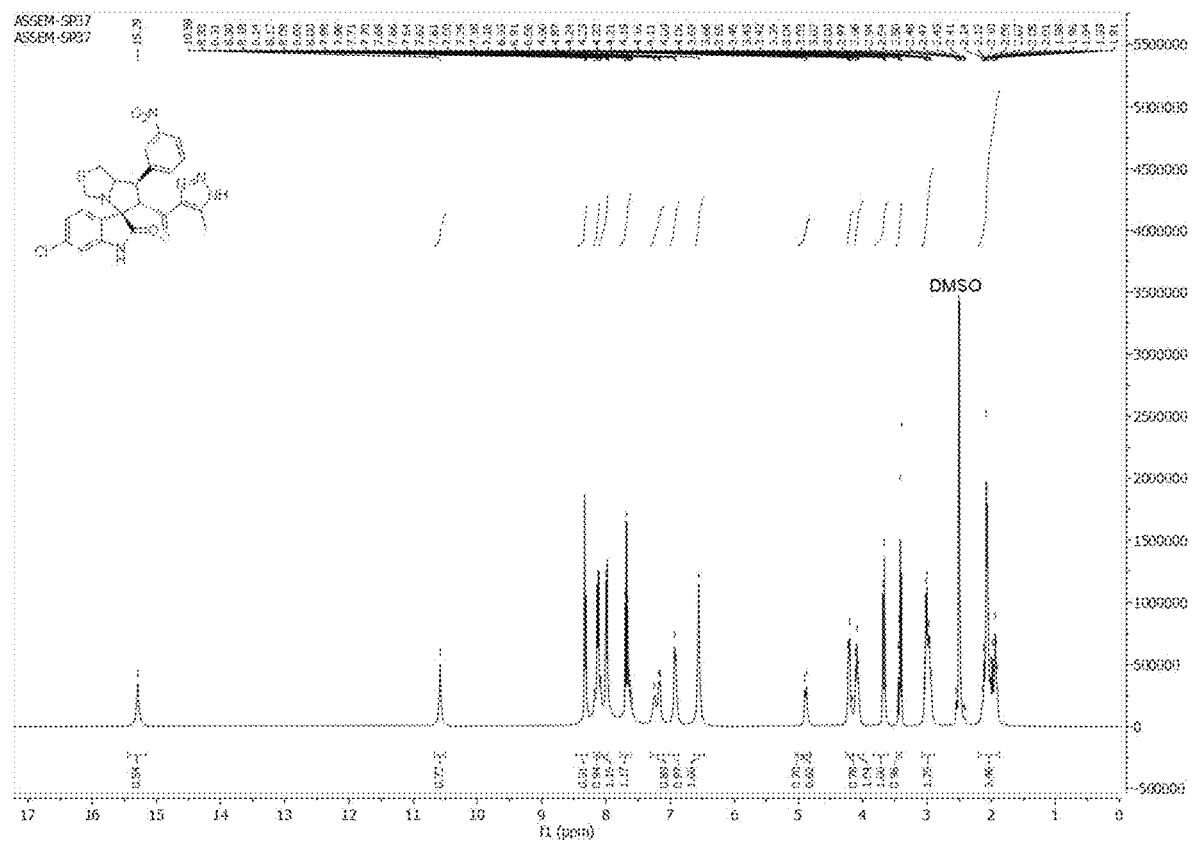
FIG. 5A is a $^1$H-NMR graph of the compound SP37.
Figure 5B:
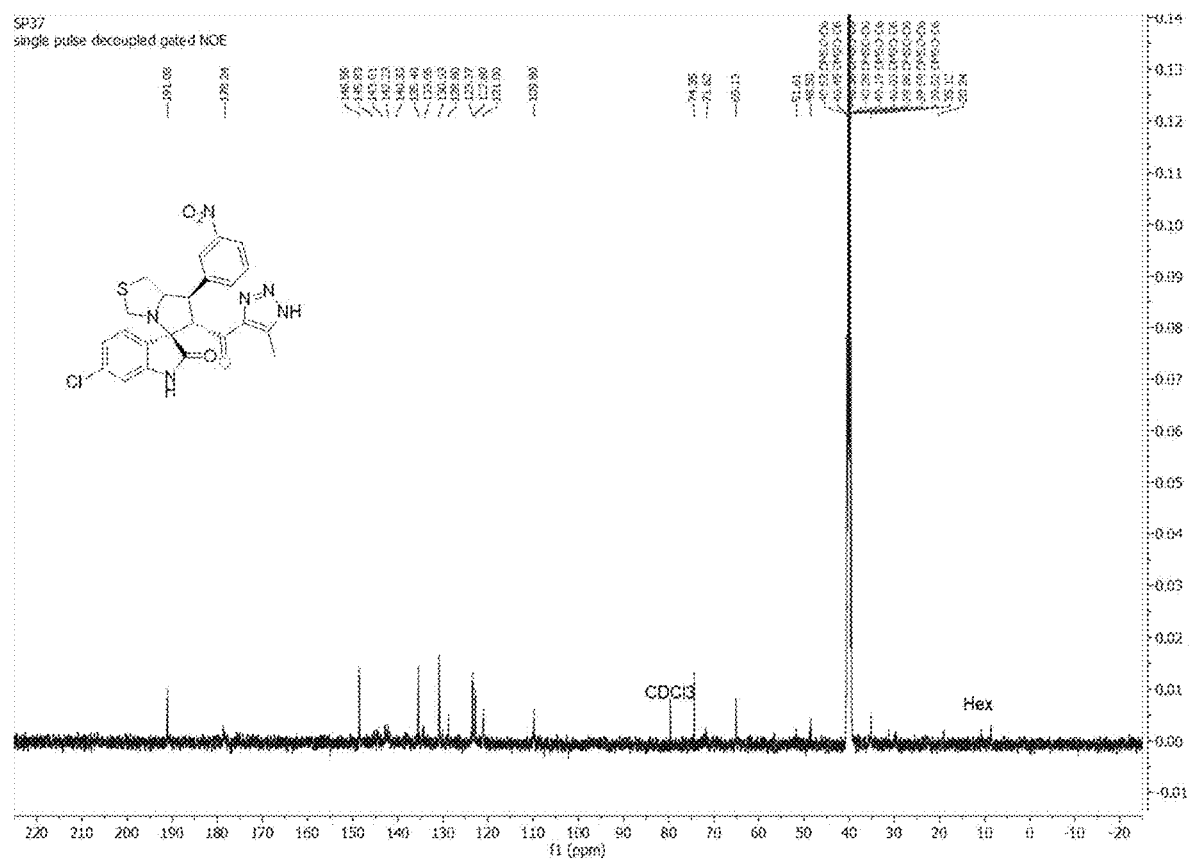
FIG. 5B is a $^{13}$C-NMR graph of the compound SP37.
Figure 6A:
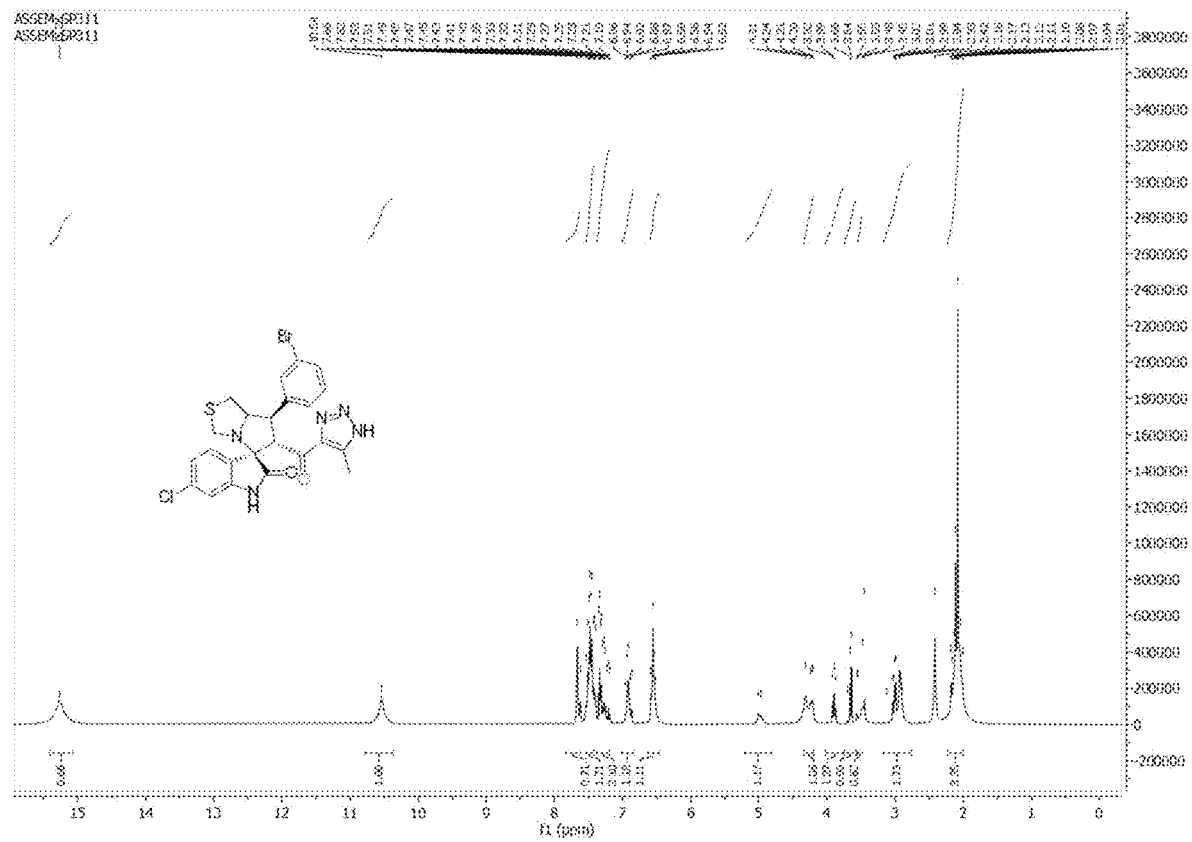
FIG. 6A is a $^1$H-NMR graph of the compound SP311.
Figure 6B:
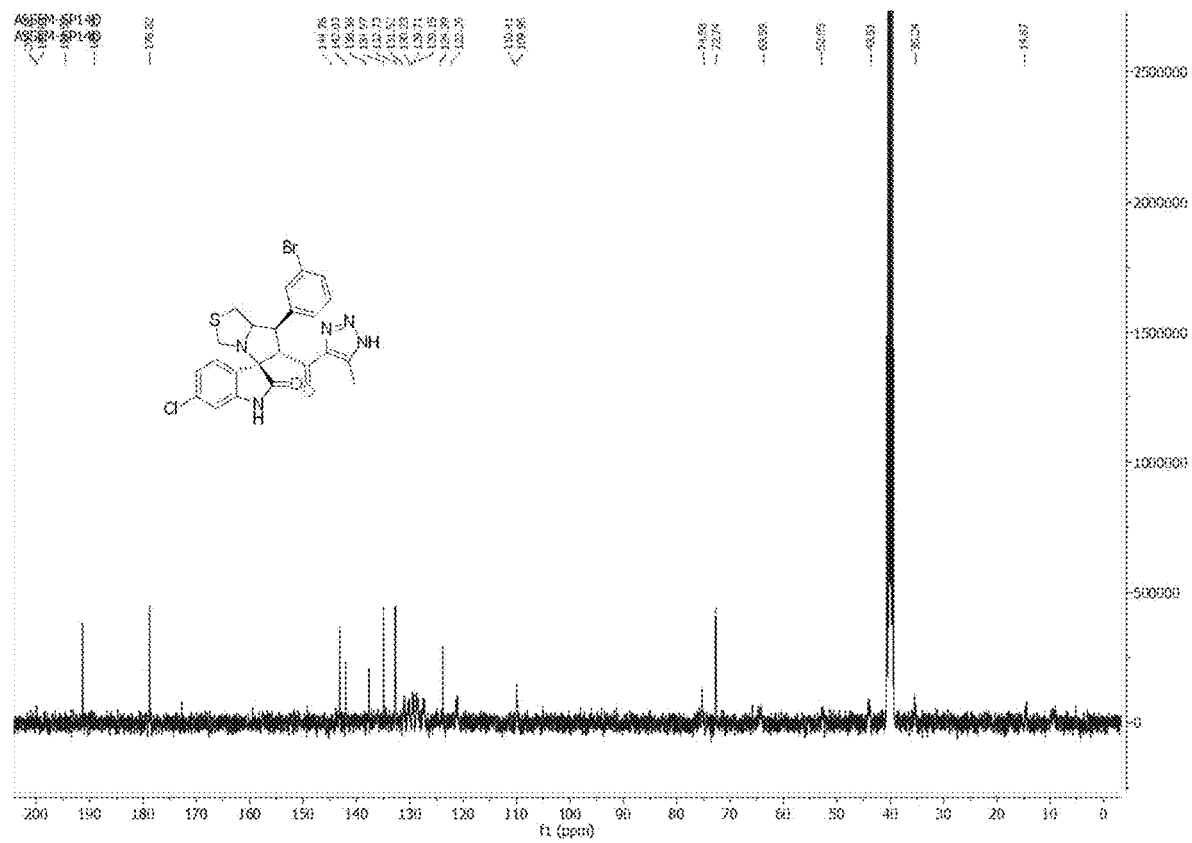
FIG. 6B is a $^{13}$C-NMR graph of the compound SP311.

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to new nitrophenyl spirooxindole derivatives that can be used as a ligand L to prepare a copper complex. The complex CuL can have much higher anticorrosion inhibitory effects than its ligand for C-steel, for example, in 1 M HCl solution.

Accordingly, in one embodiment, the present subject matter relates to a compound of the formula I:

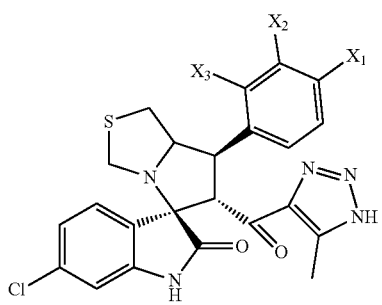

I wherein $X_1$, $X_2$, and $X_3$ are each independently selected from the group consisting of chlorine, hydrogen, $NO_2$, and bromine.

In an embodiment, the present subject matter relates to a compound of formula I, wherein $X_1$ and $X_3$ are both either hydrogen or chlorine. In another embodiment, when $X_1$ and $X_3$ are both hydrogen, $X_2$ is bromine or $NO_2$ and when $X_1$ and $X_3$ are both chlorine, $X_2$ is hydrogen.

In a further embodiment, the compound of formula I can be selected from the group consisting of:
- (3R,6'S,7'R)-6-chloro-7'-(2,4-dichlorophenyl)-6'-(5-methyl-1H-1,2,3-triazole-4-carbonyl)-1',6',7',7a'-tetrahydro-3'H-spiro[indoline-3,5'-pyrrolo[1,2-c]thiazol]-2-one (SP34);
- (3R,6'S,7'R)-6-chloro-6'-(5-methyl-1H-1,2,3-triazole-4-carbonyl)-7'-(3-nitrophenyl)-1',6',7',7a'-tetrahydro-3'H-spiro[indoline-3,5'-pyrrolo[1,2-c]thiazol]-2-one (SP37); and (3R,6'S,7'R)-7'-(3-bromophenyl)-6-chloro-6'-(5-methyl-1H-1,2,3-triazole-4-carbonyl)-1',6',7',7a'-tetrahydro-3'H-spiro[indoline-3,5'-pyrrolo[1,2-c]thiazol]-2-one (SP311).

Stated differently, the compound of formula I can be selected from the group consisting of:

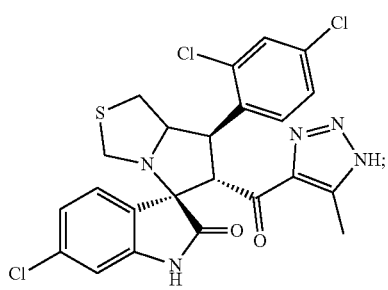

SP34

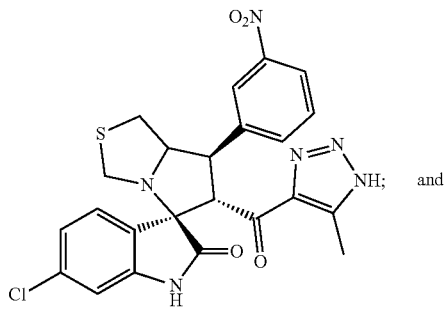

SP37 and

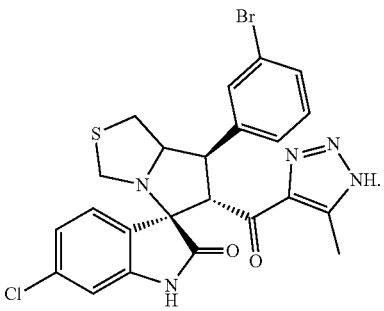

SP311

In another embodiment, the present subject matter relates to a copper complex comprising a complex of the formula II:

CuL  II wherein L is a ligand that is the compounds as described herein.

In an embodiment, the present copper complex can have an inhibition of anticorrosion of 97% or greater.

In a further embodiment, the present subject matter relates to a method for making the copper complex as described herein, the method comprising: reacting equimolar amounts (e.g., 1:1 on a molar basis) of the compound of formula I and copper chloride (CuCl) in an organic solvent; and obtaining the copper complex.

In an embodiment, the thus formed CuL copper complex can undergo anticorrosion studies by adding the obtained CuL copper complex to hydrochloric acid (for example, at 1M) using a C-steel electrode.

In another embodiment, the CuL copper complexes, where the ligand L is one of the spiro compounds SP34, SP37, or SP311, showed better inhibition of anticorrosion than the ligand L itself based on impedance and polarization studies that reached (99.2%) for the Cu-SP34 complex; (98.9%) for the Cu-SP37 complex and (97.9%) for the Cu-SP311 complex. Accordingly, in an embodiment, the CuL complex can provide a better, more rigid coat than the corresponding ligands. In general, the % inhibition of spirooxindole complexes and compounds follow the trends SP34>SP37>SP311.

In an embodiment, the present subject matter relates to an anticorrosion coating comprising the copper complex as described herein.

In a further embodiment in this regard, the anticorrosion coating, when applied to a material, can inhibit corrosion of the material, wherein the material is selected from the group consisting of steel, iron, copper, and a combination thereof. Thus, the present copper complex can provide an anticorrosion coat for steel, iron, and copper accessories, hardware, equipment, and construction materials. Further, the present anticorrosion coating can also optionally include other related organo-metallic inhibitors, or any other additives and fillers that can assist in providing coating uniformity, improve coating flow or surface drying, and/or decrease the permeability of water and/or oxygen. Further, when applied to the material, the anticorrosion coating can have a lifetime of more than 10 years. In addition, in use, a continuous monolayer of the anticorrosion coating can cover a homogeneous flat solid surface.

In one more embodiment, the present subject matter relates to a method of preventing corrosion in a material, comprising: administering a continuous monolayer of the anticorrosion coating as described herein to a material selected from the group consisting of steel, iron, copper, and a combination thereof.

In another embodiment in this regard, the material can be formed as a homogeneous flat solid surface. In a further embodiment, the material can be formed as an electrical wire, a pipe, pipeline, or piping. Suitable industries for which these materials may be of suitable interest include the oil and gas, chemical, petrochemical, infrastructure, marine, power generation, and medicinal chemistry industries.

Generally stated, the present compounds can be formed according to the following synthetic methodology for preparing the present spirooxindole derivatives:

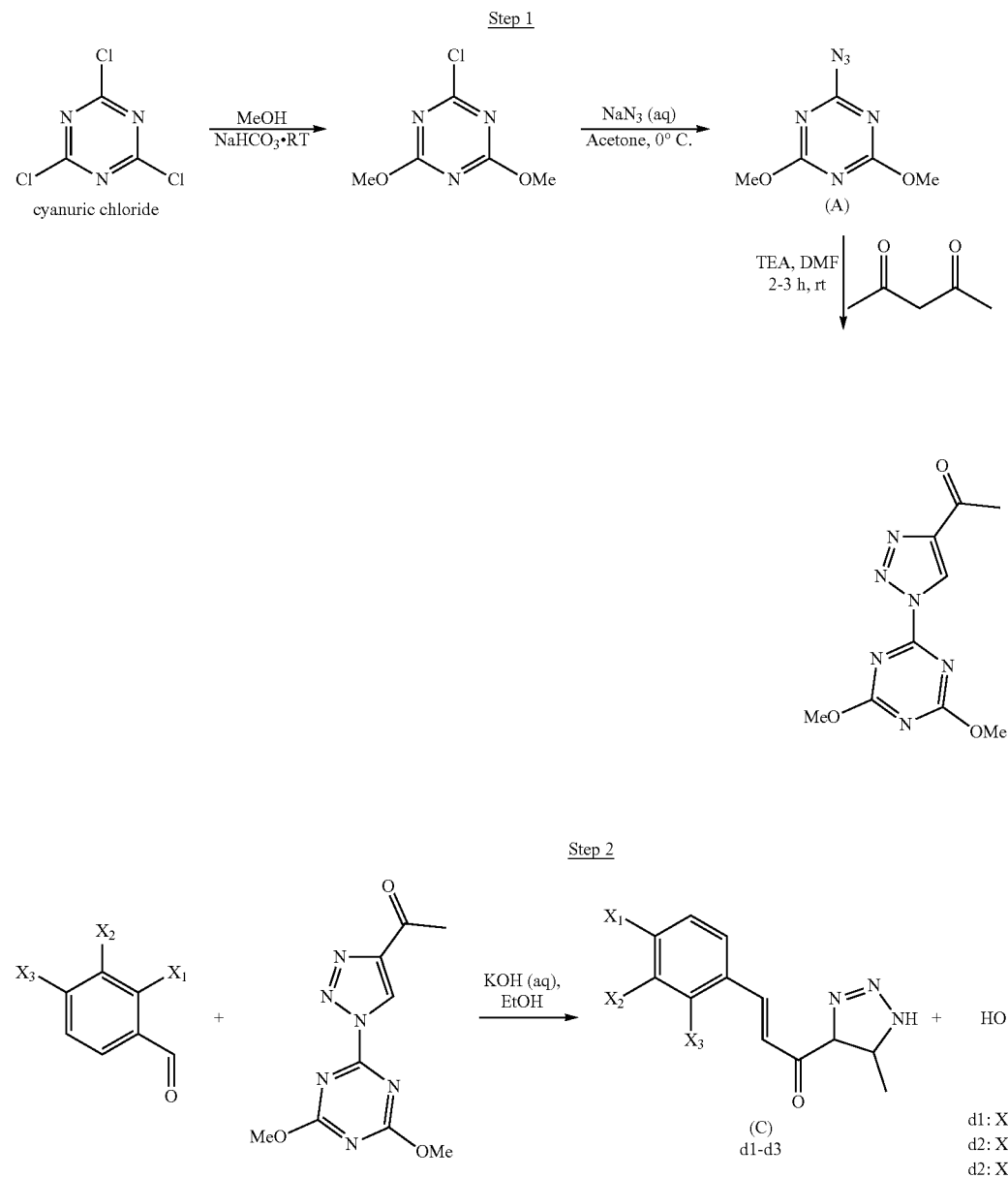

-continued

Step 3

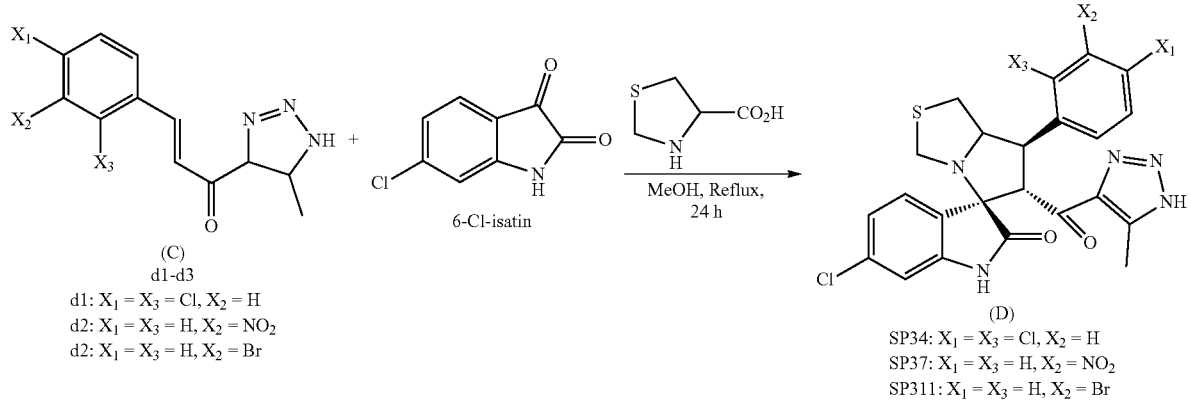

(C) d1-d3
d1: $X_1 = X_3 = Cl, X_2 = H$
d2: $X_1 = X_3 = H, X_2 = NO_2$
d2: $X_1 = X_3 = H, X_2 = Br$

6-Cl-isatin

MeOH, Reflux, 24 h (D)
SP34: $X_1 = X_3 = Cl, X_2 = H$
SP37: $X_1 = X_3 = H, X_2 = NO_2$
SP311: $X_1 = X_3 = H, X_2 = Br$ In a further embodiment, the present subject matter relates to a method of preparing the compound of formula I, the method comprising: adding about one equivalent of (s)-Thiazolidine-4-carboxylic acid to a solution of about one equivalent of a compound of formula III in an organic solvent to obtain a first mixture:

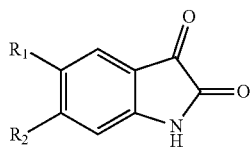

III wherein $R_1$ is selected from the group consisting of hydrogen, chlorine, fluorine, bromine, and $NO_2$ and $R_2$ is selected from the group consisting of hydrogen and chlorine; adding a chalcone of formula IV to the first mixture and refluxing for about 6 to about 12 hours to obtain a second mixture:

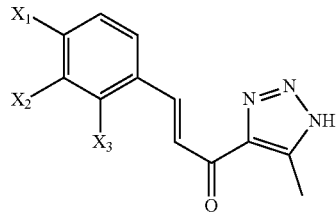

IV wherein $X_1$, $X_2$, and $X_3$ are each independently selected from the group consisting of chlorine, hydrogen, $NO_2$, and bromine; evaporating the organic solvent from the second mixture to obtain a crude product; and purifying the crude product by column chromatography to obtain the compound of formula I.

In an embodiment, the present subject matter relates to a method of preparing the compound of formula I, the method comprising: adding about one equivalent of 1-(1-(4,6-Dimethoxy-1,3,5-triazin-2-yl)-5-methyl-1H-1,2,3-triazol-4-yl) (B) to ethanol until dissolved; adding an about 7% KOH dropwise with stirring for about 5 minutes to obtain a reaction mixture; placing the reaction mixture in an ice bath and adding a benzaldehyde of formula V with stirring for about 1 to about 2 hours:

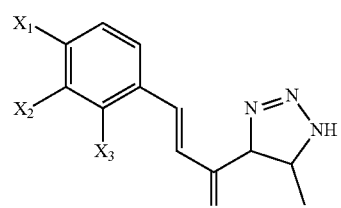

V wherein $X_1$, $X_2$, and $X_3$ are each independently selected from the group consisting of chlorine, hydrogen, $NO_2$, and bromine;
evaporating the ethanol and extracting a chalcone of formula IV:

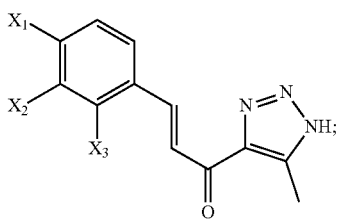

IV adding one equivalent of (s)-Thiazolidine-4-carboxylic acid to a solution of one equivalent of a compound of formula III in an organic solvent to obtain a first mixture:

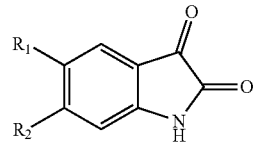

III wherein $R_1$ is selected from the group consisting of hydrogen, chlorine, fluorine, bromine, and $NO_2$ and $R_2$ is selected from the group consisting of hydrogen and chlorine; adding the chalcone of formula IV to the first mixture and refluxing for about 6 to about 12 hours to obtain a second mixture; evaporating the organic solvent from the second mixture to obtain a crude product; and purifying the crude product by column chromatography to obtain the compound of formula I.

In one more embodiment, the present subject matter relates to a method of preparing the compound of formula I, the method comprising: adding methanol to cyanuric chloride followed by NaHCO₃ with stirring at about 0° C., followed by stirring at room temperature for about 30 minutes, extraction, and drying to obtain 2,4-dichloro-6-methoxy-1,3,5-triazine; dissolving the 2,4-dichloro-6-methoxy-1,3,5-triazine in MeCn followed by adding a solution of sodium azide in water and stirring, first in an ice bath then at room temperature, extraction, concentration, and drying to obtain 2-Azido-4,6-dimethoxy-1,3,5-triazine (A); adding about one equivalent of the 2-Azido-4,6-dimethoxy-1,3,5-triazine (A) to a stirred solution of about 1.2 equivalents of acetylacetone and about 1.2 equivalents of TEA in DMF followed by adding water, filtering, and drying to obtain 1-(1-(4,6-Dimethoxy-1,3,5-triazin-2-yl)-5-methyl-1H-1,2,3-triazol-4-yl) (B); adding about one equivalent of the 1-(1-(4,6-Dimethoxy-1,3,5-triazin-2-yl)-5-methyl-1H-1,2,3-triazol-4-yl) (B) to ethanol until dissolved; adding an about 7% KOH dropwise with stirring for about 5 minutes to obtain a reaction mixture; placing the reaction mixture in an ice bath and adding a benzaldehyde of formula V with stirring for about 1 to about 2 hours:

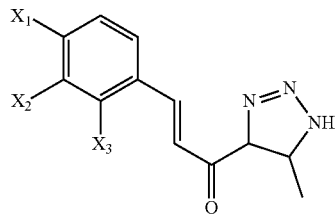

V wherein X₁, X₂, and X₃ are each independently selected from the group consisting of chlorine, hydrogen, NO₂, and bromine, evaporating the ethanol and extracting a chalcone of formula IV:

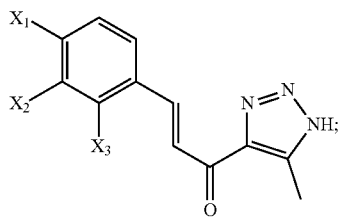

IV adding one equivalent of (s)-Thiazolidine-4-carboxylic acid to a solution of one equivalent of a compound of formula III in an organic solvent to obtain a first mixture:

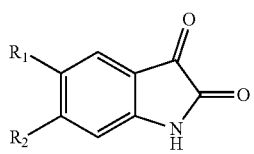

III wherein R₁ is selected from the group consisting of hydrogen, chlorine, fluorine, bromine, and NO₂ and R₂ is selected from the group consisting of hydrogen and chlorine; adding the chalcone of formula IV to the first mixture and refluxing for about 6 to about 12 hours to obtain a second mixture; evaporating the organic solvent from the second mixture to obtain a crude product; and purifying the crude product by column chromatography to obtain the compound of formula I.

In any of these production methods, in the step for obtaining the compound of formula I, the organic solvent can be, by way of non-limiting example, methanol or another suitable alcohol. Further, these production methods can each provide a yield of the compound of formula I of about 65% to about 90%.

Examples

Synthetic Examples

Example 1: General Procedure for the Synthesis of 1-(1-(4,6-dimethoxy-1,3,5-triazin-2-yl)-5-methyl-1H-1,2,3-triazol-4-yl)ethan-1-one, Formula V 150 mL of methanol was added to cyanuric chloride (16.59 g, 90 mmol) followed by NaHCO₃ (15.12 g, 180 mmol) portion wise with stirring at 0° C. The reaction mixture was further stirred at room temperature for 30 min (until the gas bubbles completely disappeared). Subsequently, excess water was added, and the reaction mixture was extracted with DCM (3×50 mL) and dried over (Na₂SO₄), after the solvent was evaporated under vacuum to get 2-chloro-4,6-dimethoxy-1,3,5-triazine as a white solid (98%): mp 86-87° C. Subsequently, 2-chloro-4,6-dimethoxy-1,3,5-triazine (2.5 g, 14 mmol) was dissolved in MeCN (100 mL) and stirred in an ice-water bath for 10 minutes. Then a solution of sodium azide (1.0 g, 15.4 mmol) in 5 mL of H₂O was added and the reaction mixture was stirred in the ice bath for 30 minutes and continued stirring at room temperature for a further 4 h. After the reaction was complete as indicated by TLC (Ethyl acetate: hexane, 1:1), the solvent was removed under vacuum at room temperature (without heating) until the volume was reduced to a quarter of its original volume. The residue was poured into water, which was extracted with DCM (3×50 mL). The combined organic phase was washed with brine (50 mL), dried over Na₂SO₄ and concentrated in vacuum to provide the pure product of 2-Azido-4,6-dimethoxy-1,3,5-triazine (A) which was employed in the next synthetic step without further purification.

2,4-Dimethoxy triazolyl-s-triazene (Formula V)) was synthesized by adding the corresponding azido-triazine derivative (Formula IV) (1 equivalent) to a stirred solution of acetylacetone (1.2 equivalent) and TEA (1.2 equivalent) in DMF. The progress of the reaction was monitored by TLC (CHCl₃/MeOH, 9:1) which showed the completion of the reaction after 2-3 hours. Excess water was then added to afford the product (B) as an off-white solid which was filtered, washed with n-hexane and dried. The yield of this reaction was 85-90% and the products were collected in their pure formulas and used directly in the next step.

1-(1-(4,6-Dimethoxy-1,3,5-triazin-2-yl)-5-methyl-1H-1,2,3-triazol-4-yl) ethan-1-one, Formula V)

The target compound of 1-(1-(4,6-dimethoxy-1,3,5-triazin-2-yl)-5-methyl-1H-1,2,3-triazol-4-yl)ethan-1-one (Formula V)) was collected as a pale-yellow solid in 90% yield; m.p. 201-203° C.; $^1$H NMR (500 MHz, CDCl$_3$) δ 4.13 (t, J=1.7 Hz, 6H, 2CH$_3$O), 3.00-2.96 (m, 3H), 2.75-2.71 (m, 3H, CH$_3$C=O); $^{13}$C NMR (126 MHz, CDCl$_3$) δ 194.40 (C=O), 173.49, 164.65 (C-Triazine), 144.14, 139.93 (2C-Triazole), 56.32 (2CH3O), 28.55 (CH$_3$C=O), 11.99 (CH$_3$-triazole); Anal. Calc. for C$_{10}$H$_{12}$N$_6$O$_3$ (264.25); C, 45.45; H, 4.58; N, 31.80. Found C, 45.33; H, 4.49; N, 31.75; HRMS-ESI (m/z) calculated for [M+H]+ 265.25; found: 265.3901.

Example 2: General Procedure for the Synthesis of Chalcones (d1-3) (GP 1)

1-(1-(4,6-Dimethoxy-1,3,5-triazin-2-yl)-5-methyl-1H-1,2,3-triazol-4-yl) (Formula V)) (1 equivalent) was added to ethanol with gentle warming until the entire amount dissolved, then 7% (w/v) KOH solution was added dropwise, and the mixture was stirred at room temperature for 5 minutes. Subsequently, the reaction mixture was placed into an ice bath and substituted benzaldehyde derivative was added portion wise while stirring for 1-2 h. The progress of the reaction was monitored by TLC (ethyl acetate/n-hexane 4:6) which showed the formation of the desired chalcones mixed with traces of side products. After the reaction was complete, the organic solvent was evaporated under vacuum and the desired product was extracted from the aqueous layer by ethyl acetate (3×15 mL). The aqueous layer was then acidified by 10% (v/v) HCl and the residual chalcone was extracted by DCM (3×15 mL). The organic solvents were dried over magnesium sulphate and evaporated under reduced pressure. The impure oily product was then purified by column chromatography (ethyl acetate-petroleum ether 3:7) to afford the target chalcones Formula VII (d1-3) as a pale-yellow solid in a good yield (60-75%).

(E)-3-(2,4-Dichlorophenyl)-1-(5-methyl-1H-1,2,3-triazol-4-yl)prop-2-en-1-one, d1

According to the general procedure (GP 1); 1-(1-(4,6-dimethoxy-1,3,5-triazin-2-yl)-5-methyl-1H-1,2,3-triazol-4-yl) ethan-1-one (Formula V) and 2,4-dichloro benzaldehyde were reacted to afford chalcone (d1) as an off-white solid in 73% yield; m.p. 220-22° C.; $^1$H NMR (400 MHz, DMSO-d$_6$) δ 7.99 (d, J 16.0 Hz, 1H), 7.95 (m, 2H), 7.66 (dt, J=14.2, 6.7 Hz, 1H), 7.44 (d, J=16.6 Hz, 1H) (3 Aromatic Protons and H-C5, H-C6), 2.34-2.47 (m, J=4.3 Hz, 3H, 3H-C1), $^{13}$C NMR (101 MHz, DMSO-d$_6$) δ 183.66 (C=O), 141.67, 139.24, 137.81, 136.64, 136.11, 135.63, 130.96, 129.52, 128.62, 123.79 (6 Aromatic C+C2,3,5,6), 28.00 (C1); Anal. Calc. for C$_{12}$H$_9$C$_{12}$N$_3$O (282.12); C, 51.09; H, 3.22; N, 14.89. Found C, 51.00; H, 3.31; N, 14.93; HRMS-ESI (m/z) calculated for [M+H]+ 283.12; found: 283.0895.

(E)-1-(5-Methyl-1H-1,2,3-triazol-4-yl)-3-(3-nitrophenyl) prop-2-en-1-one, d2

According to the general procedure (GP 1); 1-(1-(4,6-dimethoxy-1,3,5-triazin-2-yl)-5-methyl-1H-1,2,3-triazol-4-yl) ethan-1-one (Formula V) and 3-nitrobenzaldehyde were reacted to afford chalcone (d2) as a pale-yellow solid in 68% yield; m.p. 207-210° C.; $^1$H NMR (400 MHz, DMSO-d6) δ 12.51 (s, 1H, NH), 8.57 (s, 1H), 8.26 (d, J=8.7 Hz, 2H), 8.14-7.97 (m, 1H), 7.97-7.79 (m, 1H), 7.61 (dt, J=14.8, 8.4 Hz, 1H) (4 Aromatic Protons and H-C5, H—C-6), 2.43 (d, J=3.6 Hz, 3H, 3H-C1); $^{13}$C NMR (101 MHz, DMSO-d6) δ 184.17 (C=O), 149.74, 148.70 (d, J=43.3 Hz), 143.97, 140.93, 136.00, 133.79, 131.12, 126.14, 125.64, 124.13 (6 Aromatic C+C2,3,5,6), 26.95 (C1); Anal. Calc. for C$_{12}$H$_{10}$N$_4$O$_3$ (258.24); C, 55.81; H, 3.90; N, 21.70. Found C, 55.94; H, 3.79; N, 21.81; HRMS-ESI (m/z) calculated for [M+H]+ 259.24; found: 259.3074.

(E)-3-(3-Bromophenyl)-1-(5-methyl-1H-1,2,3-triazol-4-yl) prop-2-en-1-one, d3

According to the general procedure (GP 4.1); 1-(1-(4,6-dimethoxy-1,3,5-triazin-2-yl)-5-methyl-1H-1,2,3-triazol-4-yl) ethan-1-one (Formula V) and 3-bromobenzaldehyde were reacted to afford chalcone (d3) as a pale-yellow precipitate with 65% chemical yield, m.p. 193-195° C.; $^1$H NMR (500 MHz, DMSO-d6) δ 7.98 (q, J=1.8 Hz, 1H), 7.91-7.81 (m, 1H), 7.81-7.73 (m, 1H), 7.71-7.65 (m, 1H), 7.65-7.57 (m, 1H), 7.47-7.32 (m, 1H) (4 Aromatic Protons and H-C5, H—C-6), 2.40 (s, 3H, 3H-C1), $^{13}$C NMR (126 MHz, DMSO-d6) δ 183.87 (C=O), 141.51, 137.49, 136.12, 133.65, 131.70, 131.63, 131.44, 127.92, 125.02, 122.92 (6 Aromatic Carbons+C2,3,5,6), 28.07 (C1); Anal. Calc. for C$_{12}$H$_{10}$BrN$_3$O (292.14); C, 49.34; H, 3.45; N, 14.38. Found C, 49.21; H, 3.49; N, 14.50; HRMS-ESI (m/z) calculated for [M+H]+ 293.14; found: 293.2674.

Example 3: General Procedure for the Synthesis of Spirooxindole Derivatives (SP34, SP37, and SP311) (GP 4.2)

(s)-Thiazolidine-4-carboxylic acid (1 equivalent) was added to a solution of 6-chloroisatin (1 equivalent) in methanol and the mixture was stirred at room temperature for 15 minutes. Thereafter, chalcone (d1-3) was added and the reaction was refluxed in an oil bath for about 6-12 hours. Once the reaction was complete as indicated by TLC analysis (ethyl acetate/n-hexane 6:4); the solvent was evaporated under reduced pressure and the crude product was purified by column chromatography (ethyl acetate-petroleum ether 4:6) to afford the spiro derivative (SP34, SP37, and SP3111) as an off-white solid with a yield of (75-90%). In some cases, the product had oily texture after evaporating the solvent which required dissolving in diethyl ether followed by the addition of a small amount of n-hexane to afford the spiro product as an off-white precipitate which was subsequently collected by removing the solvent under vacuum.

(3R,6'S,7'R)-6-chloro-7'-(2,4-dichlorophenyl)-6'-(5-methyl-1H-1,2,3-triazole-4-carbonyl)-1',6',7',7a'-tetrahydro-3'H-spiro[indoline-3,5'-pyrrolo[1,2-c]thiazol]-2-one, SP34

The reaction of 6-chloroisatin with (S)-thiazolidine-4-carboxylic acid followed by chalcone (d1) was carried out according to the general procedure (GP 4.2). The target spiro derivative (SP34) was collected as an off-white solid in 88% yield; m.p. 199-201° C.; $^1$H NMR (400 MHz, DMSO-d$_6$) δ 15.29 (s, 1H, NH), 10.60 (s, 1H, NHC=O), 7.81 (q, J=11.5, 10.7 Hz, 1H), 7.61 (s, 1H), 7.50 (d, J=8.4 Hz, 1H), 7.10 (d, J=8.4 Hz, 1H), 6.94 (d, J=7.3 Hz, 1H), 6.55 (s, 1H) (6 aromatic protons), 4.91 (d, J=9.5 Hz, 1H, H-C5), 4.52 (t, J=8.9 Hz, 1H, H-C2), 4.06 (q, J=5.9 Hz, 1H, H-C1), 3.71 (s, 1H), 3.41 (s, 1H, H-C4), 3.09 (d, J=6.6 Hz, 1H, H-C4), 2.99-2.82 (m, 1H, H-C3), 2.05 (d, J=31.7 Hz, 3H, H—C6); $^{13}$C NMR (126 MHz, DMSO-d6) δ 191.07 (C=O), 178.88 (—NHC=O), 144.57, 137.22, 134.91, 134.59, 132.82, 130.94, 129.44, 128.90, 128.52, 122.63, 121.06, 109.95 (Aromatic Carbons), 75.07 (Shared C), 72.70 (C2), 63.94 (C4), 53.03 (C5), 44.23 (C3), 35.64 (C1), 14.48 (d, J=14.6 Hz, C6); Anal. Calc. for C$_{23}$H$_{18}$C$_{13}$N$_5$O$_2$S (534.84); C, 51.65; H, 3.39; N, 13.09. Found C, 51.59; H, 3.29; N, 13.11; HRMS-ESI (m/z) calculated for [M+H]+ 535.84; found: 535.8009.

(3R,6'S,7'R)-6-chloro-6'-(5-methyl-1H-1,2,3-triazole-4-carbonyl)-7'-(3-nitrophenyl)-1',6',7',7a'-tetrahydro-3'H-spiro[indoline-3,5'-pyrrolo[1,2-c]thiazol]-2-one, SP37

The implementation of the general procedure (GP 4.2) by involving (S)-thiazolidine-4-carboxylic acid, chalcone (d3), and 6-chloroisatin led up to the formation of the target spiro derivative (SP37) which was collected as a pale-yellow solid in 75% yield; m.p. 179-181° C.; 1H NMR (400 MHz, DMSO-$d_6$) δ 15.29 (s, 1H, NH), 10.55 (s, 1H, NHC=O), 8.32 (d, J=7.5 Hz, 1H), 8.13 (d, J=8.9 Hz, 1H), 8.10-7.97 (m, 1H), 7.66 (dt, J 14.0, 7.7 Hz, 1H), 7.30-7.10 (m, 1H), 6.92 (d, J=9.5 Hz, 1H), 6.56 (s, 1H) (7 Aromatic H), 4.88 (d, J=10.6 Hz, 1H, H-C5), 4.25-4.16 (m, 1H, H-C2), 4.11 (t, J=9.8 Hz, 1H, H—C1), 3.67 (d, J=9.0 Hz, 1H, H-C4), 3.48-3.40 (m, 1H, H-C4), 2.99 (tt, J=14.8, 7.2 Hz, 2H, H-C3), 2.11-1.86 (m, 3H, H-C6); 13C NMR (126 MHz, DMSO-d6) δ 191.08 (C=O), 178.24 (—NHC=O), 148.55, 145.83, 143.61, 142.40, 140.33, 135.48, 133.95, 130.92, 128.8, 123.37, 122.79, 121.05, 109.81 (Aromatic C), 74.35 (Shared C), 71.62 (C2), 65.13 (C4), 51.61 (C5), 48.50 (C3), 35.12 (C1), 20.24 (C6); Anal. Calc. for $C_{23}H_{19}ClN_6O_4S$ (510.95); C, 54.07; H, 3.75; N, 16.45. Found C, 54.03; H, 3.91; N, 16.50; HRMS-ESI (m/z) calculated for [M+H]+ 511.95; found: 512.1020.

(3R,6'S,7'R)-7'-(3-bromophenyl)-6-chloro-6'-(5-methyl-1H-1,2,3-triazole-4-carbonyl)-1',6',7',7a'-tetrahydro-3'H-spiro[indoline-3,5'-pyrrolo[1,2-c]thiazol]-2-one, SP311

The spiro derivative (SP311) was prepared according to the general procedure (GP 4.2) by involving chalcone (d3), 6-chloroisatin, and (S)-thiazolidine-4-carboxylic acid in the same synthetic pathway to afford the target product as an off-white solid in 73% yield; m.p. 178-182° C.; 1H NMR (400 MHz, DMSO-$d_6$) δ 15.26 (s, 1H, NH), 10.78-10.37 (m, 1H, NHC=O), 7.66 (s, 1H), 7.54-7.43 (m, 2H), 7.38-7.20 (m, 2H), 7.02-6.84 (m, 1H), 6.55 (q, J=9.8, 7.7 Hz, 1H) (7 Aromatic H), 5.16-4.70 (m, 1H, H-C5), 4.34-4.20 (m, 1H, H-C2), 3.89 (t, J=10.0 Hz, 1H, H-C1), 3.65 (d, J=9.2 Hz, 1H, H-C4), 3.55 (s, 1H, H-C4), 3.18-2.77 (m, 2H, 2H-C3), 2.08 (q, J=12.4, 11.0 Hz, 3H, 2H-C6), 13C NMR (101 MHz, DMSO-d6) δ 189.14 (C=O), 178.82 (—NHC=O), 144.76, 142.03, 138.38, 134.97, 132.73, 131.52, 130.23, 129.71, 129.15, 124.39, 122.26, 109.96 (Aromatic C), 74.88 (Shared C), 72.74 (C2), 63.59 (C4), 52.85 (C5), 43.51 (C3), 35.24 (C1), 14.87 (C6); Anal. Calc. for $C_{23}H_{19}BrClN_5O_2S$ (544.85); C, 50.70; H, 3.52; N, 12.85. Found C, 50.80; H, 3.44; N, 12.91; HRMS-ESI (m/z) calculated for [M+H]+ 545.85; found: 545.995.

Electrochemical Anticorrosion Studies

Figure 7:
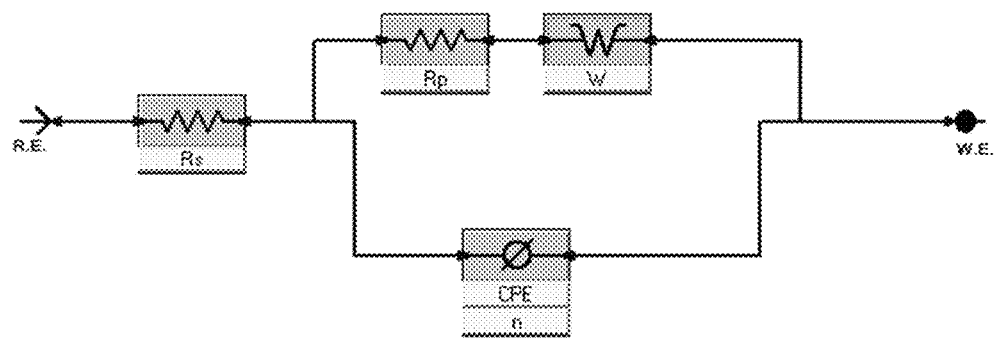
FIG. 7 shows an electrical equivalent circuit: CPE with diffusion model.

The % inhibition of Spiro compounds SP34, SP37 and SP311 and their copper complexes for C-steel in hydrochloric acid solution (1M) were computed by Impedance and Polarization studies. The model used for the electrochemical equivalent circuit to fit the impedance for anticorrosion studies of Carbon steel (C-steel) by Spiro inhibitors was CPE with diffusion as shown in FIG. 7.

Example 4: Spiro-NO$_2$ Derivative (SP 37) (L and CuL)

Figure 8:
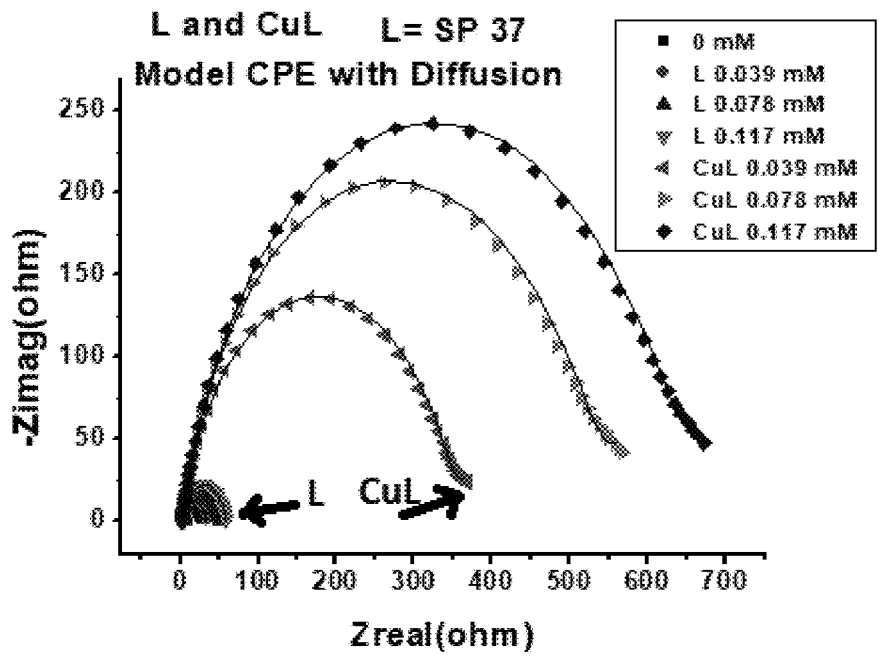
FIG. 8 is a Nyquist plot for all concentrations of Spiro-NO$_2$ SP37 (L) and (CuL) complex inhibitors in 1 M HCl for C-steel at 298 K fitted by Model CPE with Diffusion.
Figure 9:
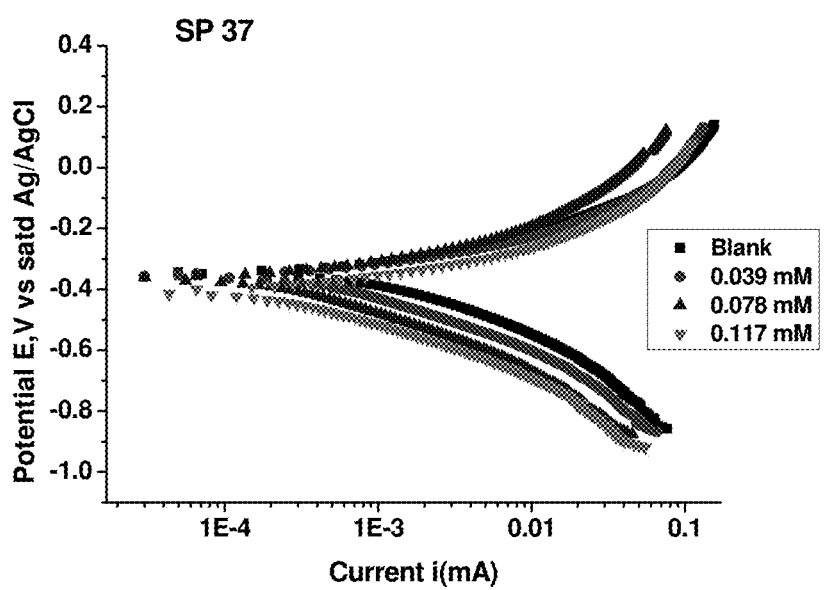
FIG. 9 is a Tafel plot for all concentrations of Spiro-NO$_2$ (SP37) inhibitors in 1 M HCl for C-steel at 298 K.
Figure 10:
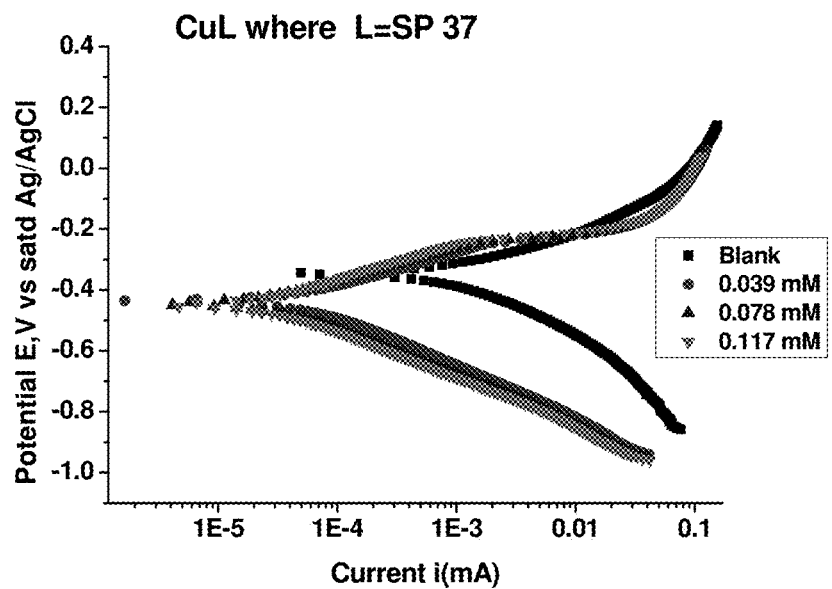
FIG. 10 is a Tafel plot for all concentrations of Spiro-NO$_2$ complex (CuL where L=SP37) inhibitor in 1 M HCl for C-steel at 298 K.

FIGS. 8-10 show a Nyquist plot for all concentrations of Spiro-NO$_2$ SP37 (L) and (CuL) complex inhibitors in 1 M HCl for C-steel at 298 K fitted by Model CPE with Diffusion; a Tafel plot for all concentrations of Spiro-NO$_2$ (SP37) inhibitors in 1 M HCl for C-steel at 298 K; and a Tafel plot for all concentrations of Spiro-NO$_2$ complex (CuL where L=SP37) inhibitor in 1 M HCl for C-steel at 298 K, respectively.

The accompanying data can be found in Tables 1-4, below.

TABLE 1

Impedance parameters for Spiro-NO$_2$ (SP 37) on the C-steel in 1M HCl medium by fitting the equivalent circuit model CPE with Diffusion.

| SP 37 Model CPE with Diffusion | Ru Ω | Ru Ω cm² | Rp Ω | Rp Ω cm² | n | $Z_{CPE}$ $Ω^{-1}s^n$ | $Z_{CPE}$ $Ω^{-1}s^n$ cm$^{-2}$ | Cdl F | Cdl μF/cm² | θ | IE % | W Ss$^{1/2}$ |
|---|---|---|---|---|---|---|---|---|---|---|---|---|
| 0 mM | 2.09 | 1.05 | 24.13 | 12.13 | 0.855 | 3.27 × 10$^{-4}$ | 6.50 × 10$^2$ | 1.44 × 10$^{-4}$ | 2.86 × 10$^2$ | 0.000 | 0.00 | 6.05 × 10$^{-1}$ |
| 0.039 mM | 2.27 | 1.14 | 30.64 | 15.40 | 0.873 | 2.30 × 10$^{-4}$ | 4.57 × 10$^2$ | 1.12 × 10$^{-4}$ | 2.23 × 10$^2$ | 0.212 | 21.25 | 1.11 × 10$^0$ |
| 0.078 mM | 4.40 | 2.21 | 45.4 | 22.82 | 0.871 | 1.67 × 10$^{-4}$ | 3.33 × 10$^2$ | 8.14 × 10$^{-5}$ | 1.62 × 10$^2$ | 0.469 | 46.85 | 1.45 × 10$^0$ |
| 0.117 mM | 2.66 | 1.34 | 55.51 | 27.90 | 0.860 | 1.59 × 10$^{-4}$ | 3.16 × 10$^2$ | 7.35 × 10$^{-5}$ | 1.46 × 10$^2$ | 0.565 | 56.53 | 3.80 × 10$^0$ |

TABLE 2

Impedance parameters for Spiro-NO$_2$ complex (CuL where L = SP 37) on the C-steel in 1M HCl medium by fitting the equivalent circuit model CPE with Diffusion.

| CuL Model CPE with Diffusion | Ru Ω | Ru Ω cm² | Rp Ω | Rp Ω cm² | n | $Z_{CPE}$ $Ω^{-1}s^n$ | $Z_{CPE}$ $Ω^{-1}s^n$ cm$^{-2}$ | Cdl F | Cdl μF/cm² | θ | IE % | W Ss$^{1/2}$ |
|---|---|---|---|---|---|---|---|---|---|---|---|---|
| 0 mM | 2.09 | 1.05 | 24.13 | 12.13 | 0.855 | 3.27 × 10$^{-4}$ | 6.50 × 10$^2$ | 1.44 × 10$^{-4}$ | 2.86 × 10$^2$ | 0.000 | 0.00 | 6.05 × 10$^{-1}$ |

TABLE 2-continued

Impedance parameters for Spiro-NO$_2$ complex (CuL where L = SP 37) on the C-steel in 1M HCl medium by fitting the equivalent circuit model CPE with Diffusion.

| CuL Model CPE with Diffusion | Ru Ω | Ru Ω cm$^2$ | Rp Ω | Rp Ω cm$^2$ | n | $Z_{CPE}$ Ω$^{-1}$s$^n$ | $Z_{CPE}$ Ω$^{-1}$s$^n$ cm$^{-2}$ | Cdl F | Cdl μF/cm$^2$ | θ | IE % | W Ss$^{1/2}$ |
|---|---|---|---|---|---|---|---|---|---|---|---|---|
| 0.039 mM | 2.22 | 1.11 | 346.8 | 174.34 | 0.847 | 7.84 × 10$^{-5}$ | 1.56 × 10$^2$ | 4.08 × 10$^{-5}$ | 8.12 × 10$^1$ | 0.930 | 93.04 | 4.40 × 10$^{-2}$ |
| 0.078 mM | 2.12 | 1.07 | 531.3 | 267.08 | 0.838 | 7.44 × 10$^{-5}$ | 1.48 × 10$^2$ | 3.98 × 10$^{-5}$ | 7.91 × 10$^1$ | 0.955 | 95.46 | 2.67 × 10$^{-2}$ |
| 0.117 mM | 1.90 | 0.96 | 636.6 | 320.02 | 0.826 | 7.52 × 10$^{-5}$ | 3.96 × 10$^{-5}$ | 1.50 × 10$^2$ | 7.87 × 10$^1$ | 0.962 | 96.21 | 2.68 × 10$^{-2}$ |

TABLE 3

Polarization parameters for various concentrations of Spiro-NO$_2$ (SP 37) on the C-steel in 1M HCl.

| SP 37 | βa V/decade | βc V/decade | I corr mA | Ecorr mV | Corrosion Rate mpy | Chi Squared | I corr mA/cm$^2$ | θ | IE % |
|---|---|---|---|---|---|---|---|---|---|
| 0 mM | 0.2295 | 0.3074 | 1918.0 | −345.8 | 1743 | 16.65 | 3815.40 | 0.000 | 0.0 |
| 0.039 mM | 0.2062 | 0.2714 | 978.2 | −356.4 | 889.1 | 30.29 | 1945.89 | 0.490 | 49.0 |
| 0.078 mM | 0.204 | 0.2582 | 524.1 | −365.3 | 476.4 | 26.51 | 1042.57 | 0.727 | 72.7 |
| 0.117 mM | 0.1768 | 0.2218 | 343.0 | −409.6 | 311.8 | 51.95 | 682.32 | 0.821 | 82.1 |

TABLE 4

Polarization parameters for various concentrations of Spiro-NO$_2$ complex (CuL) where L = SP 37 on the C-steel in 1M HCl.

| CuL | βa V/decade | βc V/decade | I corr mA | Ecorr mV | Corrosion Rate mpy | Chi Squared | I corr mA/cm$^2$ | θ | IE % |
|---|---|---|---|---|---|---|---|---|---|
| 0 mM | 0.2295 | 0.3074 | 1918.0 | −345.8 | 1743 | 16.65 | 3815.40 | 0.000 | 0.0 |
| 0.039 mM | 0.1395 | 0.1780 | 64.6 | −436.5 | 58.7 | 27.87 | 128.45 | 0.966 | 96.6 |
| 0.078 mM | 0.1310 | 0.1639 | 35.2 | −444.9 | 31.99 | 28.77 | 70.02 | 0.982 | 98.2 |
| 0.117 mM | 0.1220 | 0.1508 | 20.6 | −450.4 | 18.73 | 41.48 | 41.00 | 0.989 | 98.9 |

Example 5: Spiro-NO$_2$ Derivative (SP 37) (L and CuL)

Figure 11A:
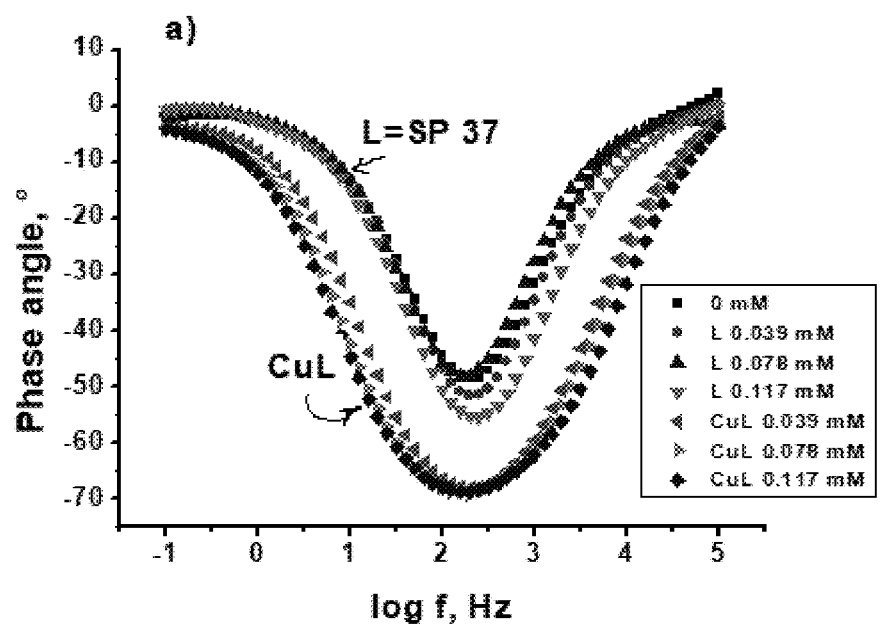
FIGS. 11A-B are Bode phase (FIG. 11A) and Bode (FIG. 11B) plots of a C-steel electrode in 1 M HCl solution with and without different concentrations of Spiro-NO$_2$ (L and CuL).
Figure 11B:
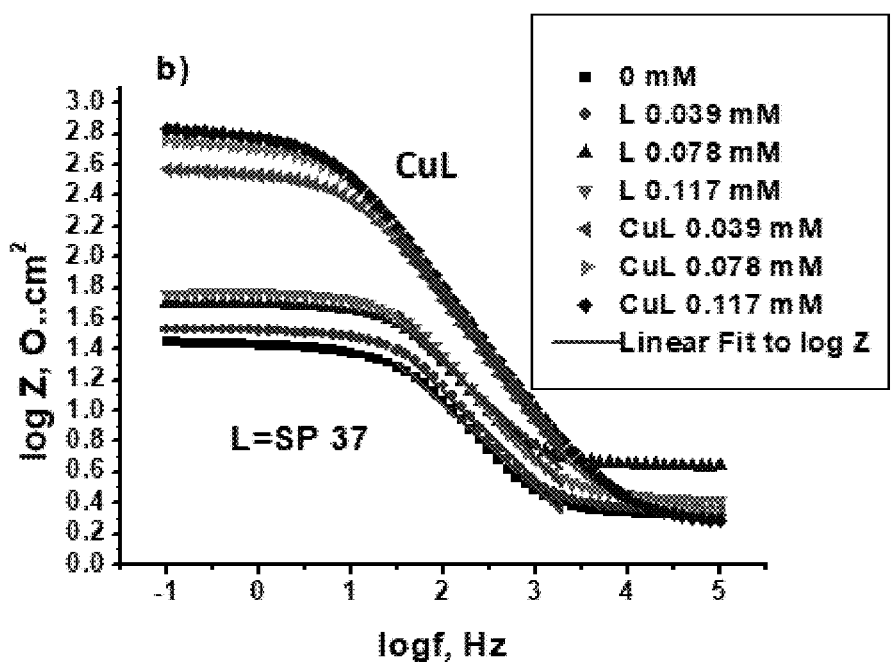

FIGS. 11A-B are Bode phase (FIG. 11A) and Bode (FIG. 11B) plots of a C-steel electrode in 1 M HCl solution with and without different concentrations of Spiro-NO$_2$ (L and CuL).

The accompanying data can be found in Table 5, below.

TABLE 5

Phase angles and alpha values (slopes) from the Bode phase and Bode plots for Spiro-NO$_2$ (L and CuL) at various concentrations.

| | | 0 mM | 0.039 mM | 0.078 mM | 0.117 mM |
|---|---|---|---|---|---|
| SP 37 | Phase angle ° | −55.42 | −51.61 | −48.21 | −55.42 |
| | Frequency Hz | 252.40 | 198.60 | 158.40 | 252.40 |
| | Slope α | −0.5434 | −0.5819 | −0.5309 | −0.6332 |
| | R$^2$ | 0.9902 | 0.9914 | 0.9855 | 0.9949 |
| CuL | Phase angle ° | −55.42 | −68.16 | −69.06 | −68.78 |
| | Frequency Hz | 252.40 | 198.60 | 198.60 | 158.40 |
| | Slope α | −0.5434 | −0.7804 | −0.7865 | −0.7800 |
| | R$^2$ | 0.9902 | 0.9994 | 0.9996 | 0.9997 |

Example 6: Spiro-di-Cl Derivative (SP 34) (L and CuL)

Figure 12:
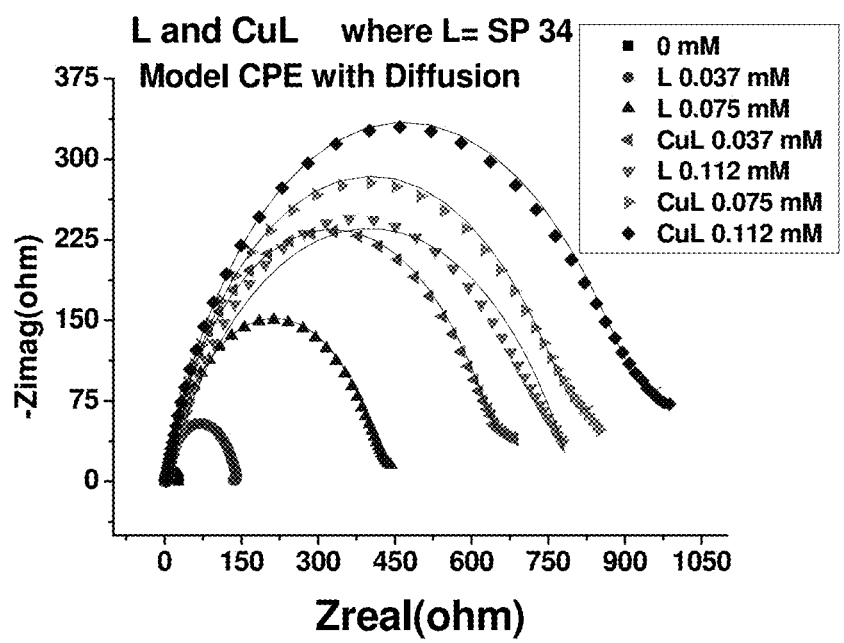
FIG. 12 is a Nyquist plot for all concentrations of Spiro-di-Cl (L=SP34) (L and CuL) inhibitors in 1 M HCl for C-steel at 298 K fitted by Model CPE with Diffusion.
Figure 13:
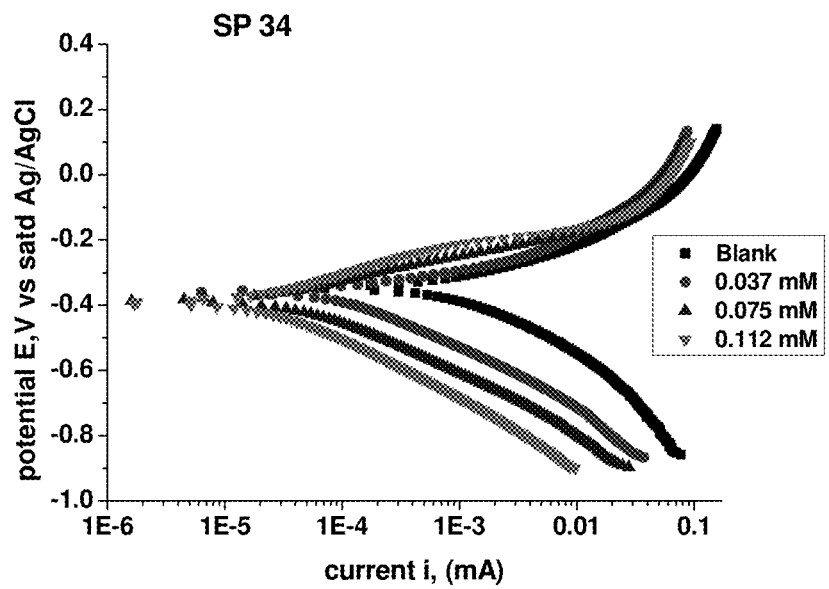
FIG. 13 is a Tafel plot for all concentrations of Spiro-di-Cl (SP34) inhibitors for C-steel in 1 M HCl at 298 K.
Figure 14:
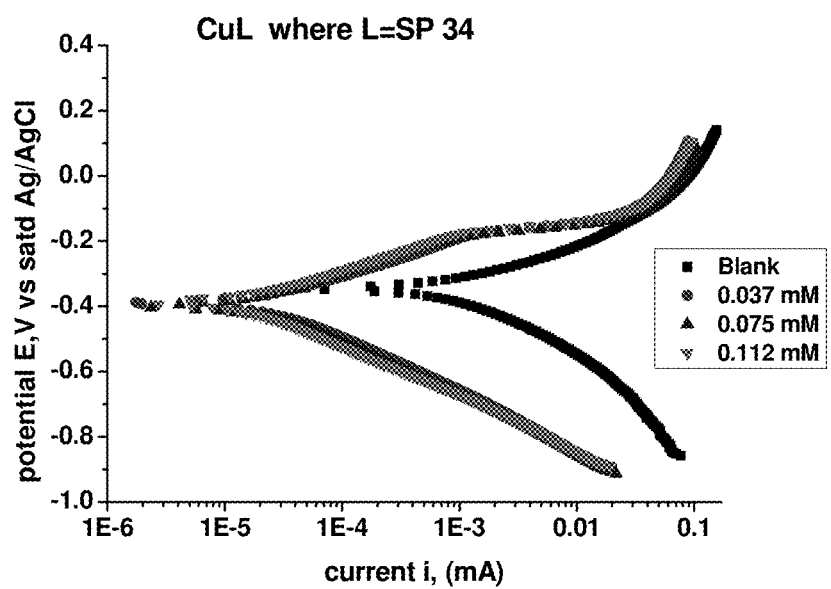
FIG. 14 is a Tafel plot for all concentrations of Spiro-di-Cl (CuL, L=SP34) inhibitors for C-steel in 1 M HCl at 298 K.

FIGS. 12-14 show a Nyquist plot for all concentrations of Spiro-di-Cl SP34 (L) and (CuL) complex inhibitors in 1 M HCl for C-steel at 298 K fitted by Model CPE with Diffusion; a Tafel plot for all concentrations of Spiro-di-Cl (SP34) inhibitors in 1 M HCl for C-steel at 298 K; and a Tafel plot for all concentrations of Spiro-di-Cl complex (CuL where L=SP34) inhibitor in 1 M HCl for C-steel at 298 K, respectively.

The accompanying data can be found in Tables 6-9, below.

TABLE 6

Impedance parameters for Spiro-di Cl (SP 34) on the C-steel in 1M HCl medium by fitting the equivalent circuit model CPE with Diffusion.

| SP 34 Model CPE with Diffusion | Rs $\Omega$ | Rs $\Omega\ cm^2$ | Rp $\Omega$ | Rp $\Omega\ cm^2$ | n | $Z_{CPE}$ $\Omega^{-1}s^n$ | $Z_{CPE}$ $\Omega^{-1}s^n\ cm^{-2}$ | Cdl F | Cdl $\mu F/cm^2$ | $\theta$ | IE % | W $Ss^{1/2}$ |
|---|---|---|---|---|---|---|---|---|---|---|---|---|
| 0 mM | 2.09 | 1.05 | 24.13 | 12.13 | 0.855 | $3.27 \times 10^{-4}$ | $6.50 \times 10^{2}$ | $1.44 \times 10^{-4}$ | $2.86 \times 10^{2}$ | 0.000 | 0.00 | 6.05E−01 |
| 0.037 mM | 2.94 | 1.48 | 137.7 | 69.22 | 0.839 | $7.09 \times 10^{-5}$ | $1.41 \times 10^{2}$ | $2.90 \times 10^{-5}$ | $5.78 \times 10^{1}$ | 0.825 | 82.48 | 1.27E+04 |
| 0.075 mM | 2.65 | 1.33 | 419.5 | 210.88 | 0.797 | $5.10 \times 10^{-5}$ | $1.01 \times 10^{2}$ | $1.92 \times 10^{-5}$ | $3.81 \times 10^{1}$ | 0.942 | 94.25 | 5.50E−02 |
| 0.112 mM | 2.37 | 1.19 | 916.1 | 460.52 | 0.798 | $4.07 \times 10^{-5}$ | $8.10 \times 10^{1}$ | $1.77 \times 10^{-5}$ | $3.52 \times 10^{1}$ | 0.974 | 97.37 | $1.39 \times 10^{-2}$ |

TABLE 7

Impedance parameters for Spiro-di-Cl complex (CuL, where L = SP 34) on the C-steel in 1M HCl medium by fitting the equivalent circuit model CPE with Diffusion.

| CuL Model CPE with Diffusion | Ru $\Omega$ | $\Omega\ cm^2$ | Rp $\Omega$ | Rp $\Omega\ cm^2$ | n | $Z_{CPE}$ $\Omega^{-1}s^n$ | $Z_{CPE}$ $\Omega^{-1}s^n\ cm^{-2}$ | Cdl F | Cdl $\mu F/cm^2$ | $\theta$ | IE % | W $Ss^{1/2}$ |
|---|---|---|---|---|---|---|---|---|---|---|---|---|
| 0 mM | 2.09 | 1.05 | 24.13 | 12.13 | 0.855 | $3.27 \times 10^{-4}$ | $6.50 \times 10^{2}$ | $1.44 \times 10^{-4}$ | $2.86 \times 10^{2}$ | 0.000 | 0.00 | $6.05 \times 10^{-1}$ |
| 0.037 mM | 2.60 | 1.31 | 642.7 | 323.09 | 0.801 | $3.86 \times 10^{-5}$ | $7.68 \times 10^{1}$ | $1.54 \times 10^{-5}$ | $3.07 \times 10^{1}$ | 0.962 | 96.25 | $2.51 \times 10^{-2}$ |
| 0.075 mM | 2.24 | 1.12 | 791.5 | 397.89 | 0.788 | $4.05 \times 10^{-5}$ | $8.05 \times 10^{1}$ | $1.61 \times 10^{-5}$ | $3.20 \times 10^{1}$ | 0.970 | 96.95 | $1.67 \times 10^{-2}$ |
| 0.112 mM | 2.37 | 1.19 | 916.1 | 460.52 | 0.798 | $4.07 \times 10^{-5}$ | $8.10 \times 10^{1}$ | $1.77 \times 10^{-5}$ | $3.52 \times 10^{1}$ | 0.974 | 97.37 | $1.39 \times 10^{-2}$ |

TABLE 8

Polarization parameters for various concentrations of Spiro-di-Cl (SP 34) on the C-steel in 1M HCl.

| SP 34 | $\beta a$ V/decade | $\beta c$ V/decade | I corr mA | Ecorr mV | Corrosion Rate mpy | Chi Squared | I corr mA/cm$^2$ | $\theta$ | IE % |
|---|---|---|---|---|---|---|---|---|---|
| 0 mM | 0.2295 | 0.3074 | 1918.0 | −345.8 | 1743 | 16.65 | 3815.40 | 0.000 | 0.0 |
| 0.037 mM | 0.1677 | 0.2163 | 183.1 | −360.4 | 166.5 | 42.74 | 364.23 | 0.905 | 90.5 |
| 0.075 mM | 0.1419 | 0.1845 | 54.7 | −385.6 | 49.72 | 35.35 | 108.81 | 0.971 | 97.1 |
| 0.112 mM | 0.1291 | 0.1924 | 26.5 | −392.9 | 24.11 | 31.38 | 52.76 | 0.986 | 98.6 |

TABLE 9

Polarization parameters for various concentrations of Spiro-di-Cl complex (CuL where L = SP 34) on the C-steel in 1M HCl.

| CuL, L = SP 34 | $\beta a$ V/decade | $\beta c$ V/decade | I corr mA | Ecorr mV | Corrosion Rate mpy | Chi Squared | I corr mA/cm$^2$ | $\theta$ | IE % |
|---|---|---|---|---|---|---|---|---|---|
| 0 mM | 0.2295 | 0.3074 | 1918.0 | −345.8 | 1743 | 16.65 | 3815.40 | 0.000 | 0.0 |
| 0.037 mM | 0.1321 | 0.1773 | 28.7 | −390.5 | 26.09 | 24.6 | 57.11 | 0.985 | 98.5 |
| 0.075 mM | 0.1224 | 0.1649 | 19.1 | −399.6 | 17.34 | 26.89 | 37.94 | 0.990 | 99.0 |
| 0.112 mM | 0.1209 | 0.1604 | 15.0 | −389.3 | 13.66 | 30.28 | 29.90 | 0.992 | 99.2 |

Example 7: Spiro-di-Cl Derivative (SP 34) (L and CuL)

Figure 15A:
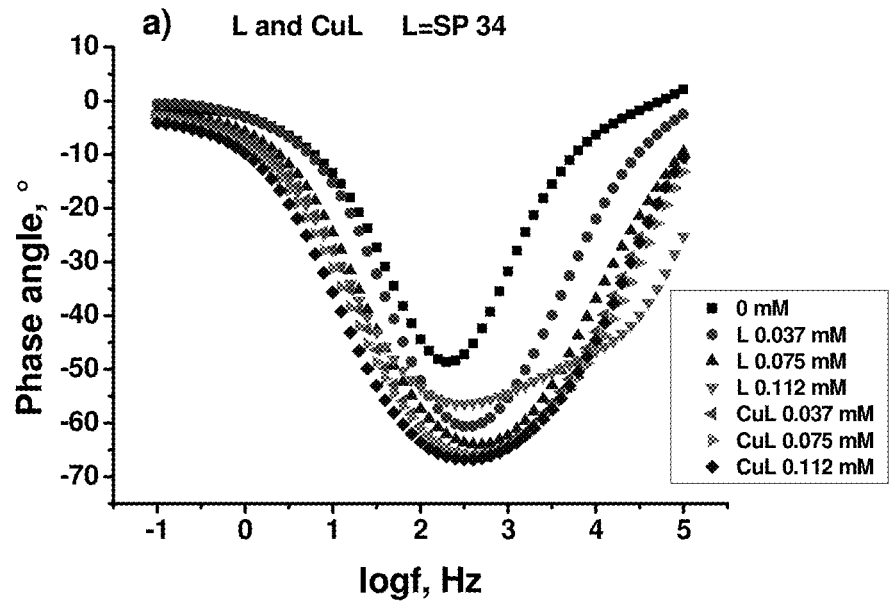
FIGS. 15A-B are Bode phase (FIG. 15A) and Bode (FIG. 15B) plots of a C-steel electrode in 1 M HCl solution with and without different concentrations of Spiro-di Cl (L and CuL, L=SP34).
Figure 15B:
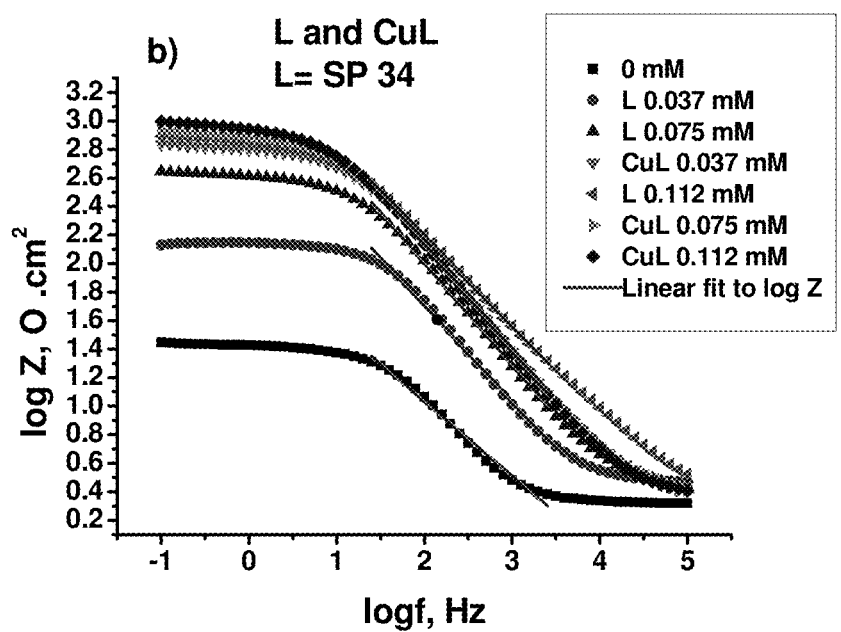

FIGS. 15A-B are Bode phase (FIG. 15A) and Bode (FIG. 15B) plots of a C-steel electrode in 1 M HCl solution with and without different concentrations of Spiro-di-Cl (L and CuL).

The accompanying data can be found in Table 10, below.

TABLE 10

Phase angles and alpha values (slopes) from the Bode phase and Bode plots for Spiro-di Cl (L and CuL, L = SP 34) at various concentrations.

| | | L = SP 34 and CuL | | | |
|---|---|---|---|---|---|
| | | 0 mM | 0.037 mM | 0.075 mM | 0.112 mM |
| SP 34 | Phase angle ° | −48.67 | −60.64 | −64.02 | −56.48 |
| | Frequency Hz | 198.60 | 315.50 | 505.50 | 315.50 |
| | Slope α | −0.5224 | −0.6717 | −0.7124 | −0.6321 |
| | $R^2$ | 0.9869 | 0.9944 | 0.9979 | 0.9995 |

TABLE 10-continued

Phase angles and alpha values (slopes) from the Bode phase and Bode plots for Spiro-di Cl (L and CuL, L = SP 34) at various concentrations.

| | | L = SP 34 and CuL | | | |
|---|---|---|---|---|---|
| | | 0 mM | 0.037 mM | 0.075 mM | 0.112 mM |
| CuL | Phase angle ° | −48.67 | −65.93 | −66.30 | −66.81 |
| | Frequency Hz | 198.60 | 398.00 | 398.00 | 315.50 |
| | Slope α | −0.5224 | −0.7371 | −0.7391 | −0.7518 |
| | $R^2$ | 0.9869 | 0.9988 | 0.9990 | 0.9996 |

Example 8: Spiro-Br Derivative (SP 311) (L and CuL)

Figure 16:
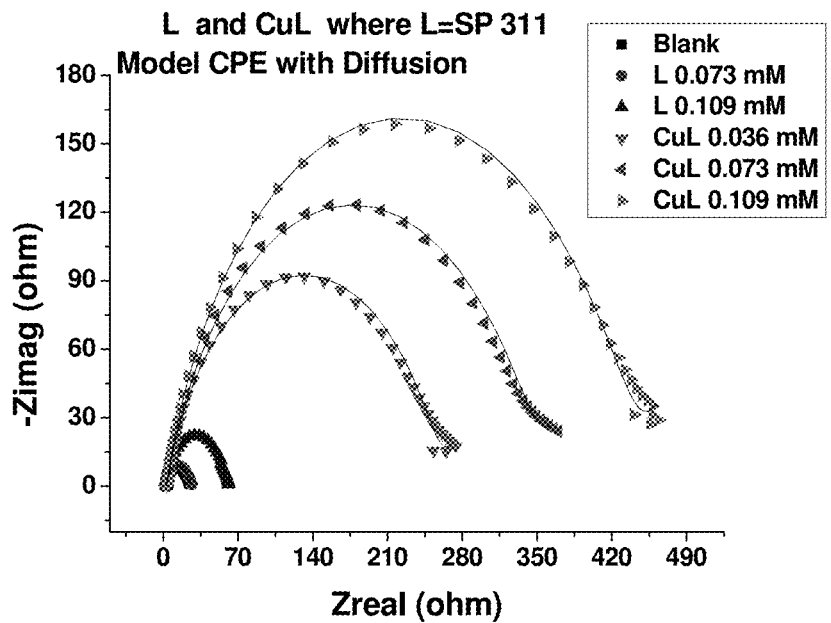
FIG. 16 is a Nyquist plot for all concentrations of Spiro-Br (L and CuL, L=SP 311) inhibitors for C-steel in 1 M HCl at 298 K fitted by Model CPE with Diffusion.
Figure 17:
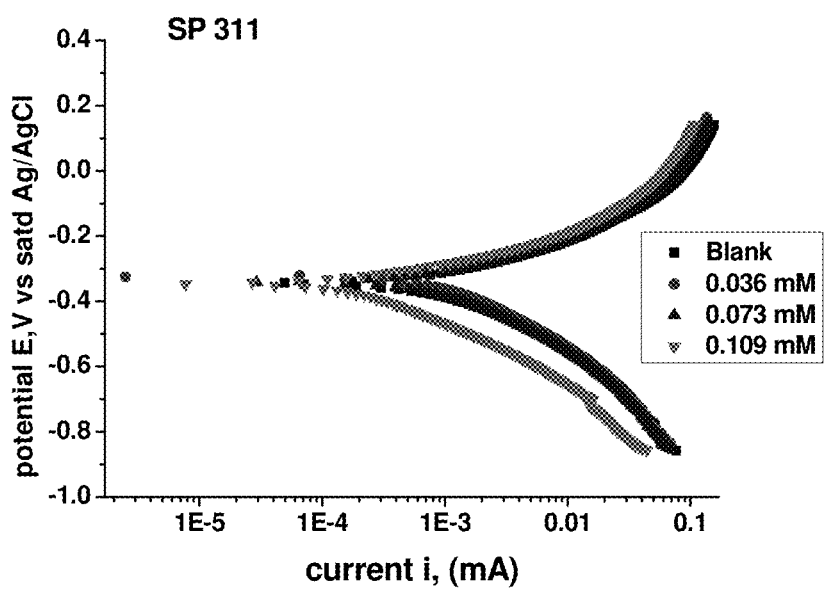
FIG. 17 is a Tafel plot for all concentrations of Spiro-Br (SP311) inhibitors for C-steel in 1 M HCl at 298 K.
Figure 18:
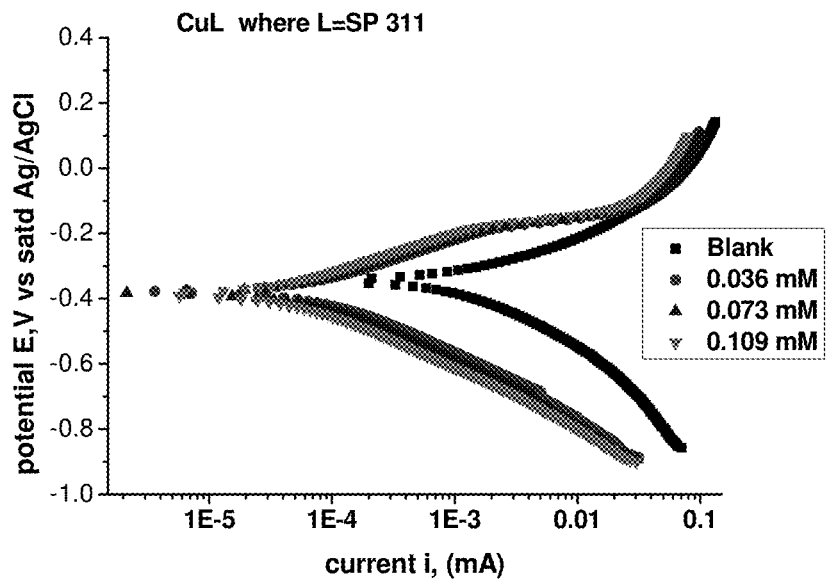
FIG. 18 is a Tafel plot for all concentrations of Spiro-Br complex (CuL where L=SP311) inhibitors for C-steel in 1 M HCl at 298 K.

FIGS. 16-18 show a Nyquist plot for all concentrations of Spiro-Br SP311 (L) and (CuL) complex inhibitors in 1 M HCl for C-steel at 298 K fitted by Model CPE with Diffusion; a Tafel plot for all concentrations of Spiro-Br (SP311) inhibitors in 1 M HCl for C-steel at 298 K; and a Tafel plot for all concentrations of Spiro-Br complex (CuL where L=SP311) inhibitor in 1 M HCl for C-steel at 298 K, respectively.

The accompanying data can be found in Tables 11-14, below.

TABLE 11

Impedance parameters for Spiro-Br (SP 311) on the C-steel in 1M HCl medium by fitting the equivalent circuit model CPE with Diffusion.

| SP 311 Model CPE with Diffusion | Rs Ω | Rs Ω cm² | Rp Ω | Rp Ω cm² | n | $Z_{CPE}$ $\Omega^{-1}s^n$ | $Z_{CPE}$ $\Omega^{-1}s^n$ cm$^{-2}$ | Cdl F | Cdl μF/cm² | θ | IE % | W Ss$^{1/2}$ |
|---|---|---|---|---|---|---|---|---|---|---|---|---|
| 0 mM | 2.52 | 1.27 | 21.23 | 10.67 | 0.855 | 3.56 × 10$^{-4}$ | 7.08 × 10$^2$ | 1.56 × 10$^{-4}$ | 3.10 × 10$^2$ | 0.000 | 0.00 | 5.42 × 10$^{-4}$ |
| 0.036 mM | 2.49 | 1.25 | 18.58 | 9.34 | 0.860 | 3.41 × 10$^{-4}$ | 6.77 × 10$^2$ | 1.49 × 10$^{-4}$ | 2.97 × 10$^2$ | 0.143 | 14.26 | 9.75 × 10$^{-1}$ |
| 0.073 mM | 2.39 | 1.20 | 23.32 | 11.72 | 0.854 | 3.26 × 10$^{-4}$ | 6.48 × 10$^2$ | 1.41 × 10$^{-4}$ | 2.81 × 10$^2$ | 0.090 | 8.96 | 9.08 × 10$^{-1}$ |
| 0.109 mM | 3.00 | 1.51 | 57.21 | 28.76 | 0.834 | 1.37 × 10$^{-4}$ | 2.72 × 10$^2$ | 5.21 × 10$^{-5}$ | 1.04 × 10$^2$ | 0.629 | 62.89 | 7.93 × 10$^{-1}$ |

TABLE 12

Impedance parameters for Spiro-Br (CuL, L = SP 311) on the C-steel in 1M HCl medium by fitting the equivalent circuit model CPE with Diffusion.

| CuL Model CPE with Diffusion | Rs Ω | Rs Ω cm² | Rp Ω | Rp Ω cm² | n | $Z_{CPE}$ $\Omega^{-1}s^n$ | $Z_{CPE}$ $\Omega^{-1}s^n$ cm$^{-2}$ | Cdl F | Cdl μF/cm² | θ | IE % | W Ss$^{1/2}$ |
|---|---|---|---|---|---|---|---|---|---|---|---|---|
| 0 mM | 2.52 | 1.27 | 21.23 | 10.67 | 0.855 | 3.56 × 10$^{-4}$ | 7.08 × 10$^2$ | 1.56 × 10$^{-4}$ | 3.10 × 10$^2$ | 0.000 | 0.00 | 5.42 × 10$^{-1}$ |
| 0.036 mM | 2.94 | 1.48 | 254.4 | 127.89 | 0.797 | 1.02 × 10$^{-4}$ | 2.03 × 10$^2$ | 4.02 × 10$^{-5}$ | 7.99 × 10$^1$ | 0.917 | 91.65 | 6.51 × 10$^{-2}$ |
| 0.073 mM | 2.65 | 1.33 | 345.1 | 173.48 | 0.786 | 9.31 × 10$^{-5}$ | 1.85 × 10$^2$ | 3.65 × 10$^{-5}$ | 7.26 × 10$^1$ | 0.938 | 93.85 | 4.71 × 10$^{-2}$ |
| 0.109 mM | 2.69 | 1.35 | 435.7 | 219.03 | 0.807 | 5.80 × 10$^{-5}$ | 1.15 × 10$^2$ | 2.28 × 10$^{-5}$ | 4.53 × 10$^1$ | 0.951 | 95.13 | 3.20 × 10$^{-2}$ |

TABLE 13

Polarization parameters for various concentrations of Spiro-Br (SP 311) on the C-steel in 1M HCl.

| SP 311 | βa V/decade | βc V/decade | I corr mA | Ecorr mV | Corrosion Rate mpy | Chi Squared | I corr mA/cm$^2$ | θ | IE % |
|---|---|---|---|---|---|---|---|---|---|
| 0 mM | 0.2468 | 0.3293 | 2237.0 | −345.9 | 2034 | 13.4 | 4449.97 | 0.000 | 0.0 |
| 0.036 mM | 0.2462 | 0.3398 | 2271.0 | −326 | 2064 | 16.74 | 4517.60 | −0.015 | −1.5 |
| 0.073 mM | 0.236 | 0.3194 | 1946.0 | −340.6 | 1769 | 16.56 | 3871.10 | 0.130 | 13.0 |
| 0.109 mM | 0.1828 | 0.247 | 412.4 | −346.5 | 374.9 | 33.61 | 820.37 | 0.816 | 81.6 |

TABLE 14

Polarization parameters for various concentrations of Spiro-Br (CuL, L = SP 311) on the C-steel in 1M HCl.

| CuL | βa V/decade | βc V/decade | I corr mA | Ecorr mV | Corrosion Rate mpy | Chi Squared | I corr mA/cm$^2$ | θ | IE % |
|---|---|---|---|---|---|---|---|---|---|
| 0 mM | 0.2468 | 0.3293 | 2237.0 | −345.9 | 2034 | 13.4 | 4449.97 | 0.000 | 0.0 |
| 0.036 mM | 0.1498 | 0.1929 | 90.8 | −378.8 | 82.56 | 27.06 | 180.68 | 0.959 | 95.9 |
| 0.073 mM | 0.1436 | 0.1875 | 67.6 | −384.1 | 61.43 | 25.7 | 134.43 | 0.970 | 97.0 |
| 0.109 mM | 0.1394 | 0.1779 | 46.0 | −386.6 | 41.83 | 23.23 | 91.55 | 0.979 | 97.9 |

Example 9: Spiro-Br Derivative (SP 311) (L and CuL)

Figure 19A:
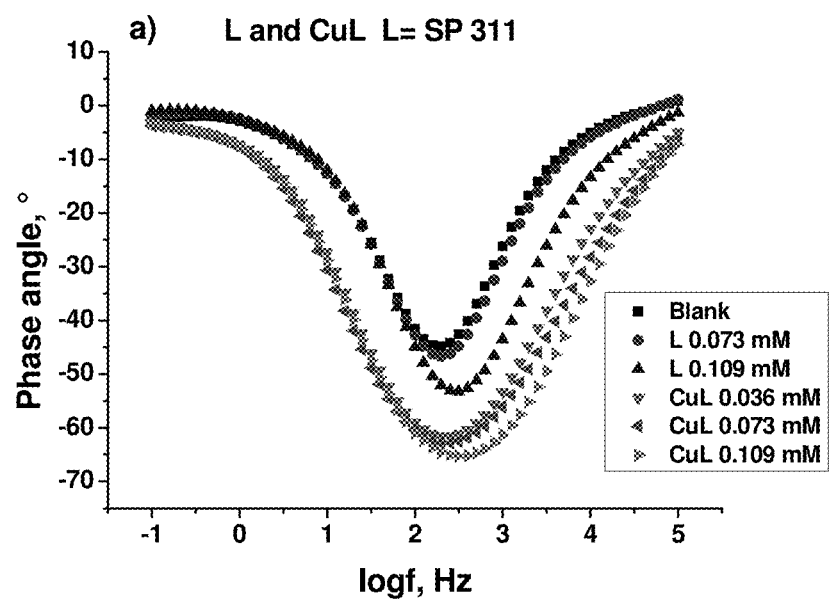
FIGS. 19A-B are Bode phase (FIG. 19A) and Bode (FIG. 19B) plots of a C-steel electrode in 1 M HCl solution with and without different concentrations of Spiro-Br (L and CuL, L=SP311).
Figure 19B:
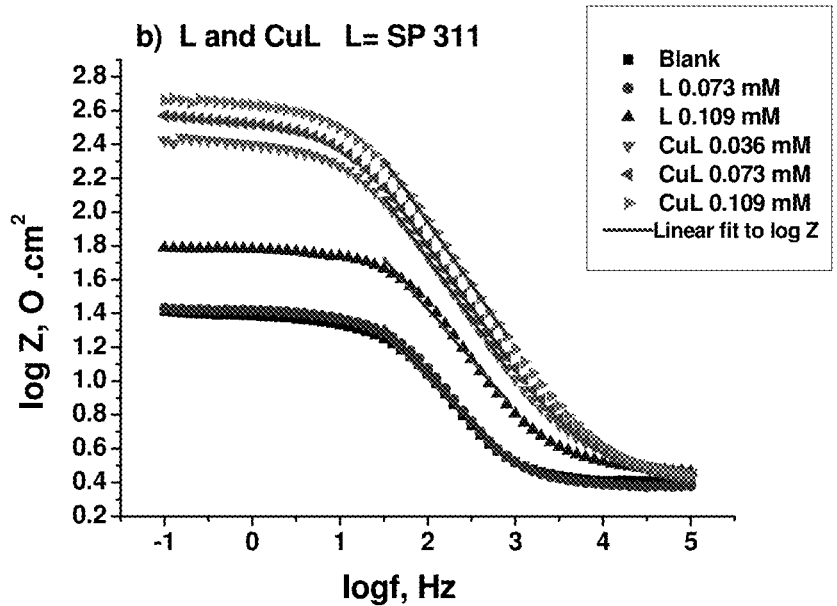

FIGS. 19A-B are Bode phase (FIG. 19A) and Bode (FIG. 19B) plots of a C-steel electrode in 1 M HCl solution with and without different concentrations of Spiro-Br (L and CuL).

The accompanying data can be found in Table 15, below.

TABLE 15

Phase angles and alpha values (slopes) from the Bode phase and Bode plots for Spiro-Br (L and CuL, L = SP 311) at various concentrations.

L = SP 311 and CuL

| | | 0 mM | 0.036 mM | 0.073 mM | 0.109 mM |
|---|---|---|---|---|---|
| SP 311 | Phase angle ° | −44.86 | −43.50 | −46.68 | −53.23 |
| | Frequency Hz | 198.60 | 198.60 | 198.60 | 315.50 |
| | Slope α | −0.5382 | −0.4465 | −0.5577 | −0.5999 |
| | R$^2$ | 0.99392 | 0.97417 | 0.99354 | 0.98763 |
| CuL | Phase angle ° | −44.86 | −61.59 | −61.09 | −61.02 |
| | Frequency Hz | 198.60 | 198.60 | 198.60 | 198.60 |
| | Slope α | −0.5382 | −0.7196 | −0.7274 | −0.7423 |
| | R$^2$ | 0.99392 | 0.9992 | 0.9995 | 0.9987 |

Example 10: Adsorption Studies

Figure 20A:
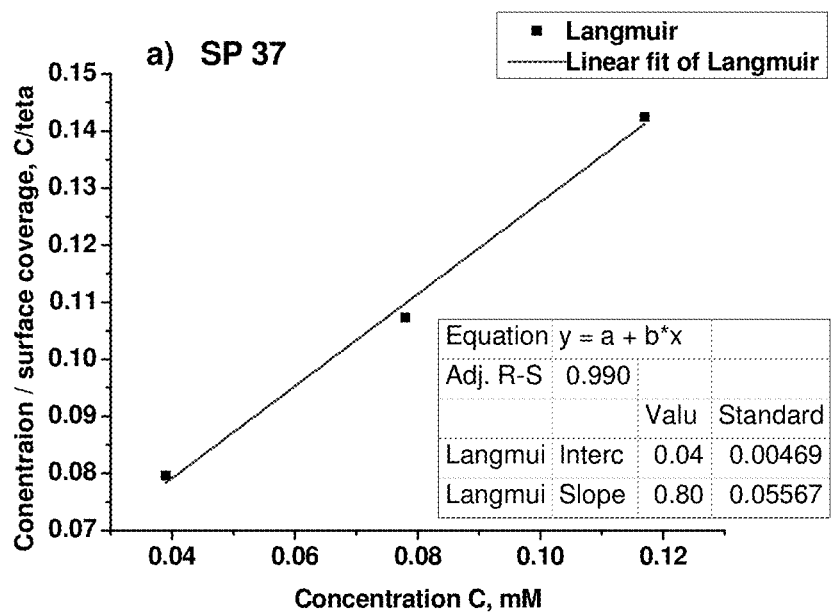
FIGS. 20A-C are adsorption isotherms from Tafel plots for SP37 on C-steel in 1 M HCl medium.
Figure 20B:
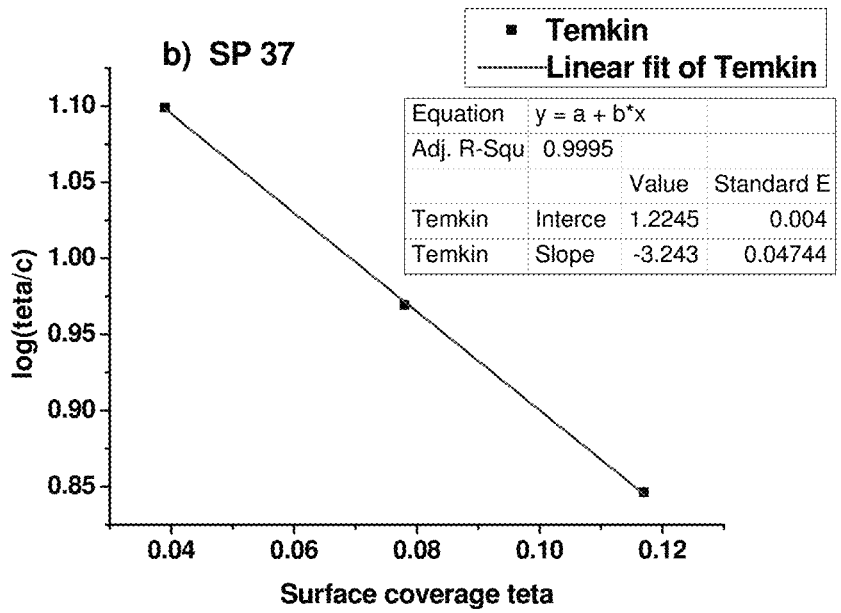
Figure 20C:
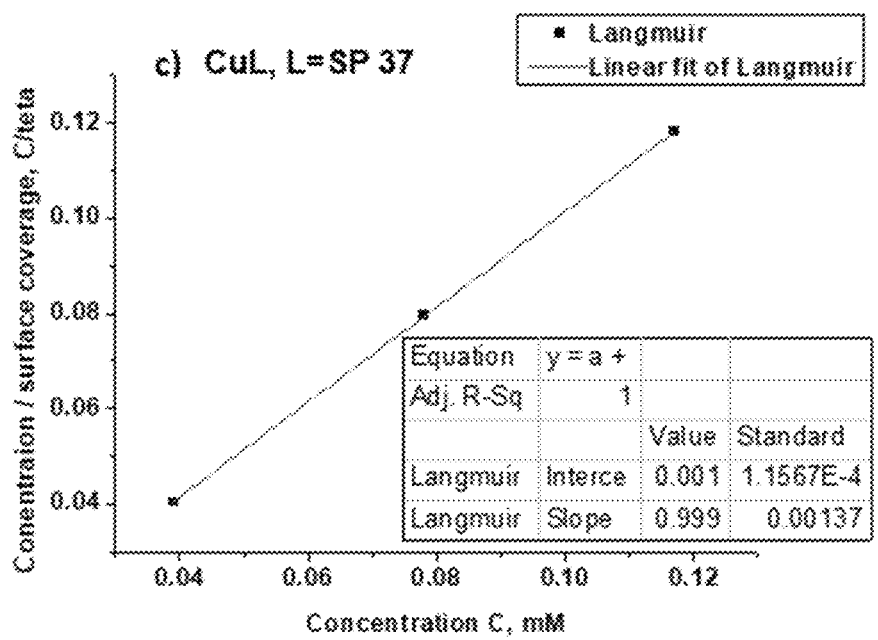
Figure 21A:
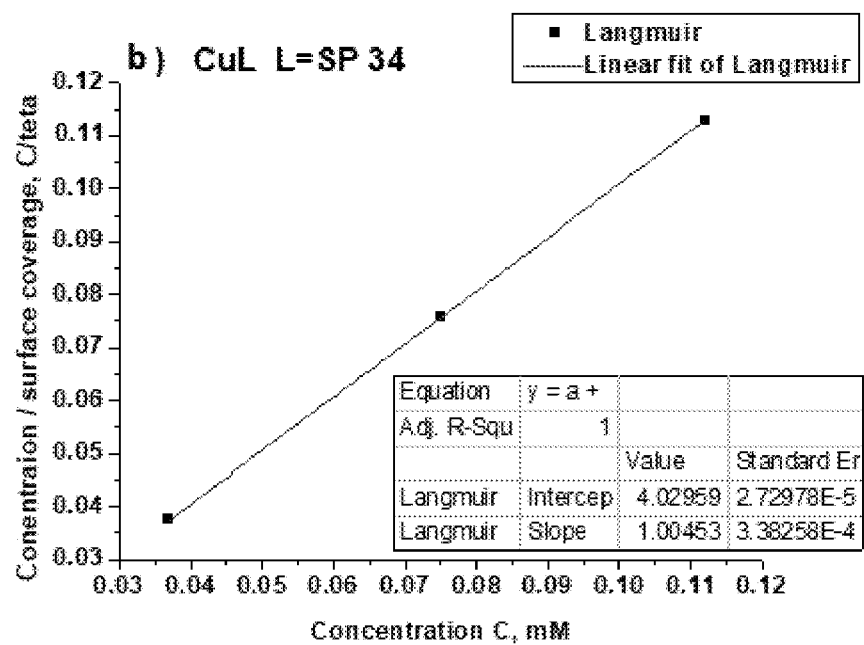
FIGS. 21A-B are adsorption isotherms from Tafel plots for (FIG. 21A) SP34 Langmuir model, and (FIG. 21B) (CuL, L=SP34) Langmuir model on C-steel in 1 M HCl medium.
Figure 21B:
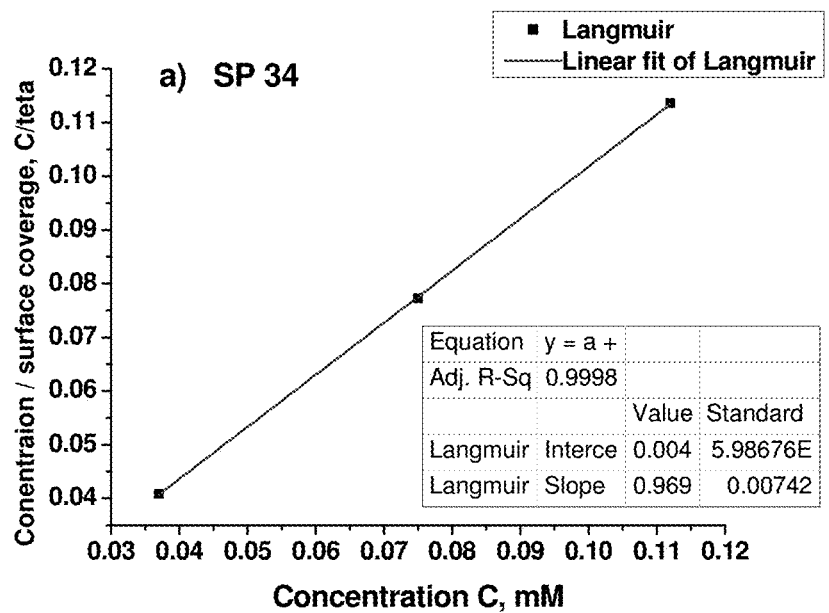
Figure 22A:
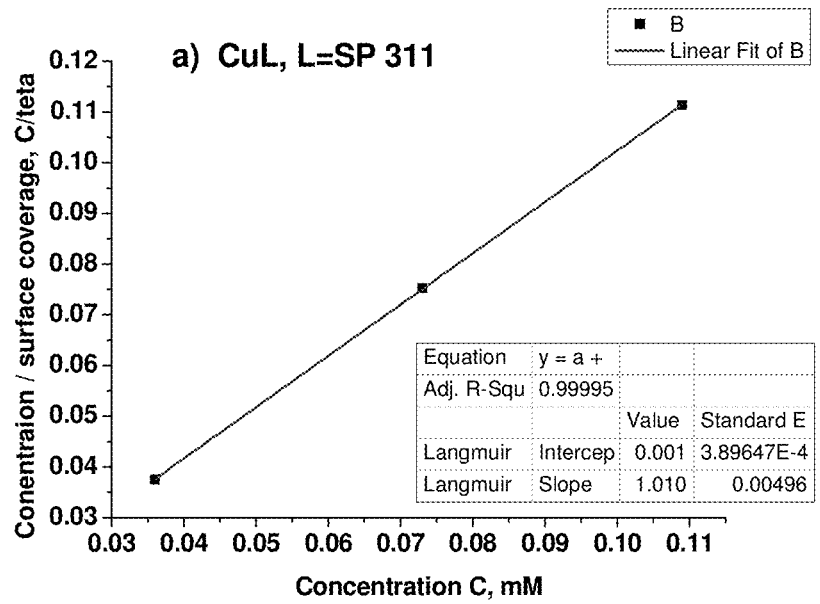
FIGS. 22A-B are adsorption isotherms from Tafel plots for (CuL, L=SP311) on C-steel in 1 M HCl medium.
Figure 22B:
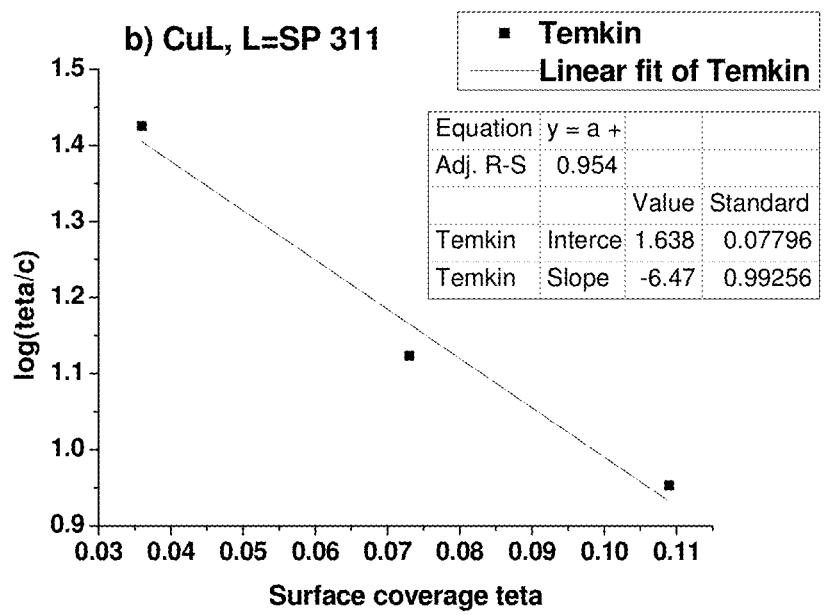

The adsorption mechanism of the inhibitors Spiro compounds and copper complexes on the surface of C-steel were studied by three models using the anticorrosion % inhibition data from Tafel plots, as shown in FIGS. 20-22.

The accompanying data, summarizing the anticorrosion results, can be found in Tables 16-18, below.

TABLE 16

| A) Samples | % inhibition from Impedance | % inhibition from Tafel | Langmuir Model (R$^2$) | Temkin Model (R$^2$) | Frumkin Model (R$^2$) |
|---|---|---|---|---|---|
| L = SP 37 | 56.53 | 82.1 | 0.9900 | 0.9995 | 0.8963 |
| L = SP 34 | 96.97 | 98.6 | 0.9998 | 0.9649 | 0.9684 |
| L = SP 311 | 62.89 | 81.6 | 0.2679 | — | — |
| CuL, SP 37 cpx | 96.21 | 98.9 | 1.00 | 0.8563 | 0.3198 |
| CuL, SP 34 cpx | 97.37 | 99.2 | 1.00 | 0.9555 | 0.9610 |
| CuL, SP 311 cpx | 95.13 | 97.9 | 0.9999 | 0.954 | 0.6368 |

TABLE 17

| B) Samples | % Inhibition from Impedance studies |
|---|---|
| L | SP 34 (96.97%) > SP 311 (62.89%) > SP 37 (56.53%) |
| CuL | CuL, SP 34 cpx (97.37%) > CuL, SP 37 cpx (96.21%) > CuL, SP 311 cpx (95.13%) |

TABLE 18

| C) Samples | % Inhibition from Tafel plots |
|---|---|
| L | SP 34 (98.6%) > SP 37 (82.1%) > SP 311 (81.6%) |
| CuL | CuL, SP 34 cpx (99.2%) > CuL, SP 37 cpx (98.9%) > CuL, SP 311 cpx (97.9%) |

It is to be understood that the spirooxindole compounds and associated copper complexes are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A compound of the formula I:

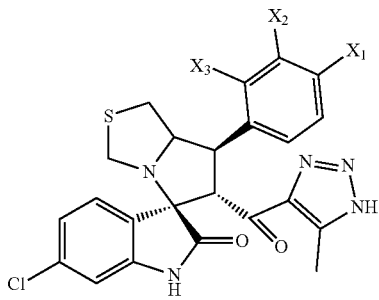

wherein $X_1$, $X_2$, and $X_3$ are each independently selected from the group consisting of chlorine, hydrogen, $NO_2$, and bromine.

2. The compound of claim 1, wherein $X_1$ and $X_3$ are both either hydrogen or chlorine.

3. The compound of claim 1, wherein when $X_1$ and $X_3$ are both hydrogen, $X_2$ is bromine or $NO_2$ and when $X_1$ and $X_3$ are both chlorine, $X_2$ is hydrogen.

4. The compound of claim 1, wherein the compound is selected from the group consisting of:
- (3R,6'S,7'R)-6-chloro-7'-(2,4-dichlorophenyl)-6'-(5-methyl-1H-1,2,3-triazole-4-carbonyl)-1',6',7',7a'-tetrahydro-3'H-spiro[indoline-3,5'-pyrrolo[1,2-c]thiazol]-2-one (SP34);
- (3R,6'S,7'R)-6-chloro-6'-(5-methyl-1H-1,2,3-triazole-4-carbonyl)-7'-(3-nitrophenyl)-1',6',7',7a'-tetrahydro-3'H-spiro[indoline-3,5'-pyrrolo[1,2-c]thiazol]-2-one (SP37); and
- (3R,6'S,7'R)-7'-(3-bromophenyl)-6-chloro-6'-(5-methyl-1H-1,2,3-triazole-4-carbonyl)-1',6',7',7a'-tetrahydro-3'H-spiro[indoline-3,5'-pyrrolo[1,2-c]thiazol]-2-one (SP311).

5. A copper complex comprising a complex of the formula II:

CuL      II wherein L is a ligand that is the compound of claim 1.

6. A method for making the copper complex of claim 5, the method comprising:
reacting equimolar amounts of the compound of claim 1 and copper chloride (CuCl) in an organic solvent; and
obtaining the copper complex.

7. An anticorrosion coating comprising the copper complex of claim 5.

8. A method of preventing corrosion in a material, comprising:
administering a continuous monolayer of the anticorrosion coating of claim 7 to a material selected from the group consisting of steel, iron, copper, and a combination thereof.

9. The method of claim 8, wherein the material is formed as a homogeneous flat solid surface.

10. The method of claim 8, wherein the material is formed as an electrical wire, a pipe, or piping.

11. A method of preparing the compound of claim 1, the method comprising:
adding about one equivalent of (s)-Thiazolidine-4-carboxylic acid to a solution of about one equivalent of a compound of formula III in an organic solvent to obtain a first mixture:

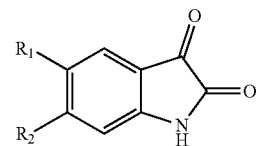

wherein $R_1$ is selected from the group consisting of hydrogen, chlorine, fluorine, bromine, and $NO_2$ and $R_2$ is selected from the group consisting of hydrogen and chlorine;
adding a chalcone of formula IV to the first mixture and refluxing for about 6 to about 12 hours to obtain a second mixture:

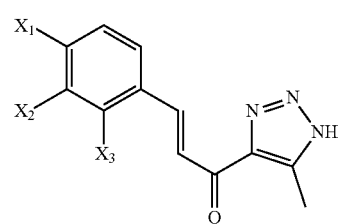

wherein $X_1$, $X_2$, and $X_3$ are each independently selected from the group consisting of chlorine, hydrogen, $NO_2$, and bromine;
evaporating the organic solvent from the second mixture to obtain a crude product; and
purifying the crude product by column chromatography to obtain the compound of claim 1.

12. The method of claim 11, wherein the organic solvent is methanol.

13. The method of claim 11, wherein a yield of the compound of claim 1 is about 65% to about 90%.

14. A method of preparing the compound of claim 1, the method comprising:
adding about one equivalent of 1-(1-(4,6-Dimethoxy-1,3,5-triazin-2-yl)-5-methyl-1H-1,2,3-triazol-4-yl) (B) to ethanol until dissolved;
adding an about 7% KOH dropwise with stirring for about 5 minutes to obtain a reaction mixture;
placing the reaction mixture in an ice bath and adding a benzaldehyde of formula V with stirring for about 1 to about 2 hours:

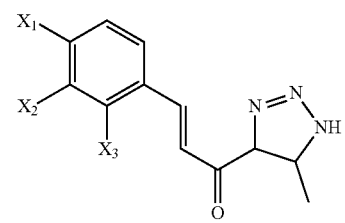

wherein $X_1$, $X_2$, and $X_3$ are each independently selected from the group consisting of chlorine, hydrogen, $NO_2$, and bromine;

evaporating the ethanol and extracting a chalcone of formula IV:

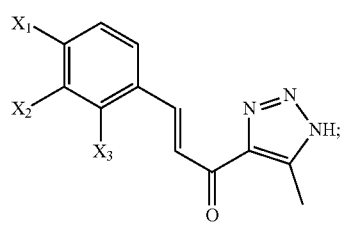

adding one equivalent of (s)-Thiazolidine-4-carboxylic acid to a solution of one equivalent of a compound of formula III in an organic solvent to obtain a first mixture:

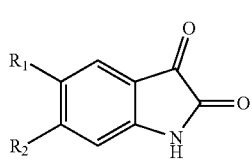

wherein $R_1$ is selected from the group consisting of hydrogen, chlorine, fluorine, bromine, and $NO_2$ and $R_2$ is selected from the group consisting of hydrogen and chlorine;

adding the chalcone of formula IV to the first mixture and refluxing for about 6 to about 12 hours to obtain a second mixture;

evaporating the organic solvent from the second mixture to obtain a crude product; and purifying the crude product by column chromatography to obtain the compound of claim 1.

15. A method of preparing the compound of claim 1, the method comprising:

adding methanol to cyanuric chloride followed by $NaHCO_3$ with stirring at about 0° C., followed by stirring at room temperature for about 30 minutes, extraction, and drying to obtain 2,4-dichloro-6-methoxy-1,3,5-triazine;

dissolving the 2,4-dichloro-6-methoxy-1,3,5-triazine in MeCn followed by adding a solution of sodium azide in water and stirring, first in an ice bath then at room temperature, extraction, concentration, and drying to obtain 2-Azido-4,6-dimethoxy-1,3,5-triazine (A);

adding about one equivalent of the 2-Azido-4,6-dimethoxy-1,3,5-triazine (A) to a stirred solution of about 1.2 equivalents of acetylacetone and about 1.2 equivalents of TEA in DMF followed by adding water, filtering, and drying to obtain 1-(1-(4,6-Dimethoxy-1,3,5-triazin-2-yl)-5-methyl-1H-1,2,3-triazol-4-yl) (B);

adding about one equivalent of the 1-(1-(4,6-Dimethoxy-1,3,5-triazin-2-yl)-5-methyl-1H-1,2,3-triazol-4-yl) (B) to ethanol until dissolved;

adding an about 7% KOH dropwise with stirring for about 5 minutes to obtain a reaction mixture;

placing the reaction mixture in an ice bath and adding a benzaldehyde of formula V with stirring for about 1 to about 2 hours:

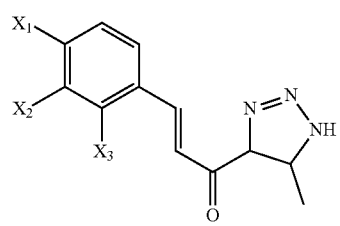

wherein $X_1$, $X_2$, and $X_3$ are each independently selected from the group consisting of chlorine, hydrogen, $NO_2$, and bromine;

evaporating the ethanol and extracting a chalcone of formula IV:

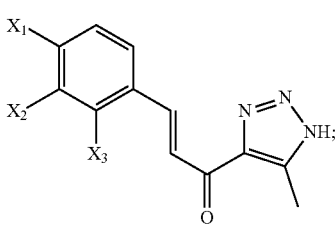

adding one equivalent of (s)-Thiazolidine-4-carboxylic acid to a solution of one equivalent of a compound of formula III in an organic solvent to obtain a first mixture:

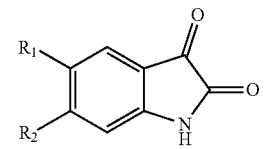

wherein $R_1$ is selected from the group consisting of hydrogen, chlorine, fluorine, bromine, and $NO_2$ and $R_2$ is selected from the group consisting of hydrogen and chlorine;

adding the chalcone of formula IV to the first mixture and refluxing for about 6 to about 12 hours to obtain a second mixture;

evaporating the organic solvent from the second mixture to obtain a crude product; and purifying the crude product by column chromatography to obtain the compound of claim 1.

16. The method of claim 15, wherein a yield of the compound of claim 1 is about 65% to about 90%.

* * * * *